United States Patent
Craven

(10) Patent No.: US 9,724,337 B2
(45) Date of Patent: Aug. 8, 2017

(54) AG-205 FOR THE TREATMENT OF BREAST CANCER

(75) Inventor: Rolf Joseph Craven, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 360 days.

(21) Appl. No.: 12/763,676

(22) Filed: Apr. 20, 2010

(65) Prior Publication Data
US 2010/0266540 A1  Oct. 21, 2010

Related U.S. Application Data

(60) Provisional application No. 61/171,164, filed on Apr. 21, 2009.

(51) Int. Cl.
| | | |
|---|---|---|
| *A61K 31/428* | (2006.01) | |
| *A61K 31/437* | (2006.01) | |
| *A61K 31/4375* | (2006.01) | |
| *A61K 31/655* | (2006.01) | |
| *A61P 35/00* | (2006.01) | |
| *A61K 31/519* | (2006.01) | |
| *A61K 31/65* | (2006.01) | |
| *A61K 31/661* | (2006.01) | |
| *A61K 45/06* | (2006.01) | |

(52) U.S. Cl.
CPC .......... *A61K 31/437* (2013.01); *A61K 31/428* (2013.01); *A61K 31/4375* (2013.01); *A61K 31/519* (2013.01); *A61K 31/65* (2013.01); *A61K 31/655* (2013.01); *A61K 31/661* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,485,045 A | 11/1984 | Regen | |
| 4,544,545 A | 10/1985 | Ryan et al. | |
| 6,027,726 A | 2/2000 | Ansell | |
| 6,139,869 A | 10/2000 | Hosokawa et al. | |
| 7,342,100 B2 * | 3/2008 | Craven | 530/350 |

FOREIGN PATENT DOCUMENTS

EP      0 133 988 A2    3/1985

OTHER PUBLICATIONS

Yoshitani et al., A structure-based strategy for discovery of small ligands binding to functionally unknown proteins: Combination of in silico screening and surface plasmon resonance measurements, 2005, Proteomics, vol. 5, p. 1472-1480.*

Girling et al., Comparison of oral etoposide and standard intravenous multidrug chemoterhapy for small-cell lung cancer: a stopped multicentre randomised trial, 1996, The Lancet, vol. 348, p. 563-566.*
Therasse, J. Natl. Cancer Inst., vol. 92, p. 205-216, 2000.*
Fumoleua, European Journal of Cancer, vol. 40, p. 536-542, 2004.*
Milosevic, Seminars in Radiation Oncology, vol. 14, No. 3, p. 249-258, 2004.*
Celis, Molecular and Cellular Proteomics, vol. 3, p. 327-344, 2004.*
Montrose-Rafizadeh, The Journal of Biological Chemistry, vol. 272, p. 21201-21206, 1997.*
van Waarde (Biochimica et Biophysica Acta, vol. 1848, p. 2703-2714, 2015).*
"Pgrme1 (progesterone receptor membrane component 1): a heme-1 domain protein that promotes tumorigenesis and is inhibited by a small molecule", Ikhlas S. Ahmed, et al., Department of Molecular and Biomedical Pharmacology (I.S.A., H.J.R., K.E.T., M.N.M, RJ.C.), Markey Cancer Center, Univ. of Kentucky, Lexington, Kentucky, 40536; Copyright 2010 by the American Society for Pharmacology and Experimental Therapeutics, pps. (35 pages).
Yimin Liu et al., "Compartmentalization of Phosphatidylinositol 4,5-Bisphosphate in Low-Density Membrane Domains in the Absence of Caveolin" Biochemical and Biophysical Research Communications, 1998, pp. 684-690, vol. 245.
Christoph A. Ritter et al., "The Epidermal Growth Factor Receptor-Tyrosine Kinase: A Promising Therapeutic Target in Solid Tumors", Seminars in Oncology, Feb. 2003, pp. 3-11, vol. 30, No. 1, suppl 1.
John B. Schenkman et al., "The Many Roles of Cytochrome b5", Pharmacology & Therapeutics, 2003, pp. 139-152, vol. 97.
Robert Langer et al., "Biocompatibility of Polymeric Delivery Systems for Macromolecules", Journal of Biomedical Materials Research, Mar. 1981, pp. 267-277, vol. 15, No. 2.
K. Bajou et al., "Absence of Host Plasminogen Activator Inhibitor 1 Prevents Cancer Invasion and Vascularization", Nature Medicine, Aug. 1998, pp. 923-928, vol. 4, No. 8.
Ilan Bank et al., "The Epidermotropic Mycosis Fungoides Associated α1β1 Integrin (VLA-1, CD49a/CD29) is Primarily a Collagen IV Receptor on Malignant T Cells", Journal of Cutaneous Pathology, 1999, pp. 65-71, vol. 26.
J. Downward et al., "Close Similarity of Epidermal Growth Factor Receptor and v-erb-B Oncogene Protein Sequences" Nature, Feb. 1984, pp. 521-527, vol. 307, No. 5951.
Kenneth R. Sidman et al., "Controlled Relsease of Macromolecules and Pharmaceuticals from Synthetic Polypeptides Based on Glutamic Acid", Biopolymers, Jan. 1983, pp. 547-556, vol. 22.
Robert Langer, "Controlled Release of Macromolecules", Chemtech, Feb. 1982, pp. 98-105.
Dirk Gerdes et al., "Cloning and Tissue Expression of Two Putative Steroid Membrane Receptors", Biol. Chem., Jul. 1998, pp. 907-911, vol. 379.

(Continued)

*Primary Examiner* — Michael D Allen
(74) *Attorney, Agent, or Firm* — Crowell & Moring LLP

(57) ABSTRACT

Compositions, methods, and combination therapies for the treatment of cancers, including lymphomas, leukemias, melanomas, lung cancer, and metastatic disease, are provided. Specifically, compositions comprising ligands to Pgrmc1 are disclosed for use in treating and inhibiting tumor growth and progression and inhibition of metastases. The compositions and methods using these ligands can be used alone or in combination with other reagents and cancer treatment modalities.

8 Claims, 9 Drawing Sheets

(56) References Cited

OTHER PUBLICATIONS

Pier Paolo Di Fiore et al., "Overexpression of the Human EGF Receptor Confers an EGF-Dependent Transformed Phenotype to NIH 3T3 Cells", Cell , Dec. 1987, pp. 1063-1070, vol. 51.
David S. Salomon et al., "Epidermal Growth Factor-Related Peptides and Their Receptors in Human Malignancies", Critical Reviews in Oncology/Hematology, 1995, pp. 183-232, vol. 19.
W. G. Cance et al., "Expression Polymerase Chain Reaction: A Sensitive Method for Analysis of Gene Expression in Human Tumours", Surg Oncol, 1992, pp. 309-314, vol. 1.
T. A. Bramley et al., "Non-Genomic Steroid Receptors in the Bovine Ovary", Domestic Animal Endocrinology, 2002, pp. 3-12, vol. 23.
Jikui Song et al., "Letter to the Editor: Hypothetical Protein At2g24940.1 from Arabidopsis thaliana has a Cytochrome b5 Like Fold", Journal of Biomolecular NMR:, 2004, pp. 215-218, vol. 30.
Sinto Sebastian et al., "The Complexity of Targeting EGFR Signalling in Cancer: From Expression to Turnover", Biochimica et Biophysica Acta, 2006, pp. 120-139, vol. 1766.
Mitsugi Furukawa et al., "Gefitinib-Sensitive EGFR Lacking Residues 746-750 Exhibits hypophosphorylation at Tyrosine Residue 1045, Hypoubiquitination, and Impaired Endocytosis", DNA and Cell Biology, 2007, pp. 178-185, vol. 26, No. 3.
Michael A. Cahill "Progesterone Receptor Membrane Component 1: An Integrative Review", Journal of Steroid Biochemistry & Molecular Biology, 2007, pp. 16-36, vol. 105.
Ikuo Kimura et al., "Neurotrophic Activity of Neudesin, A Novel Extracellular Heme-Binding Protein, Is Dependent on the Binding of Heme to Its Cytochrome b5-Like Heme/Steroid-Binding Domain", The Journal of Biological Chemistry, Feb. 2008, pp. 4323-4331, vol. 283, No. 7.
Rolf J. Craven et al., "Regulation of Iron Homeostasis Mediated by the Heme-Binding Protein Dap1 (Damage Resistance Protein 1) Via the P450 Protein Erg11/Cyp51", The Journal of Biological Chemistry, Dec. 2007, pp. 36543-36551, vol. 282, No. 50.
John J. Peluso et al., "Regulation of Ovarian Cancer Cell Viability and Sensitivity to Cisplatin by Progesterone Receptor Membrane Component-1", J. Clin Endocrinol Metab., May 2008, pp. 1592-1599, vol. 93, No. 5.
Kaushik Ghosh et al., "Spectroscopic and Biochemical Characterization of Heme Binding to Yeast Dap1P and Mouse PGRMC1p", Biochemistry, Dec. 2005, pp. 16729-16736, vol. 44, No. 50.
William Mifsud et al., "Membrane-Bound Progesterone Receptors Contain a Cytochrome b5-Like Ligand-Binding Domain", Genome Biology, 2002, vol. 3, No. 12.
Li Min et al., "Molecular Identification of Adernal Inner Zone Antigen as a Heme-Binding Protein", FEBS Journal, vol. 272, 2005, pp. 5832-5843.
Christiane Meyer et al., "Purification and Partial Sequencing of High-Affinity Progesterone-Binding Site(s) From Porcine Liver Membranes", Eur. J. Biochem., 1996, pp. 726-731, vol. 239.
Gerard Crudden et al., "Overexpression of the Cytochrome P450 Activator Hpr6 (Heme-1 Domain Protein/Human Progesterone Receptor) in Tumors", Tumor Biol., 2005, vol. 26, pp. 142-146.
Rolf J. Craven et al., "PGRMC1: A New Biomarker for the Estrogen Receptor in Breast Cancer", Breast Cancer Research, 2008, vol. 10.
Adam L. Hughes et al., "Dap1/PGRMC1 Binds and Regulates Cytochrome P450 Enzymes", Cell Metabolism, Feb. 2007, pp. 143-149, vol. 5.
Hannah J. Rohe et al., "PGRMC1 (Progesterone Receptor Membrane Component 1): A Targetable Protein with Multiple Functions in Steroid Signaling, P450 Activation and Drug Binding", Pharmacology & Therapeutics, 2009, pp. 14-19, vol. 121.
Joseph E. De Larco et al., "Sarcoma Growth Factor from Mouse Sarcoma Virus-Transformed Cells", The Journal of Biological Chemistry, Apr. 1980, pp. 3685-3690, vol. 255, No. 8.
Jan Brabender et al., "Epidermal Growth Factor Receptor and HER2-neu mRNA Expression in Non-Small Cell Lung Cancer is Correlated with Survival", Clinical Cancer Research, Jul. 2001, pp. 1850-1855, vol. 7.

Mayumi Ono et al., "Molecular Mechanisms of Epidermal Growth Factor Receptor (EGFR) Activation and Response to Gefitinib and Other EGFR-Targeting Drugs", Clinical Cancer Recearch, Dec. 2006, pp. 7242-7251, vol. 12, No. 24.
M. A. Bareschino et al., "Erlotinib in Cancer Treatment", Annals of Oncology, 2007, pp. vi35-vi41, vol. 18, suppl. 6.
Roy S. Herbst et al., "Tribute: A Phase III Trial of Erlotinib Hydrochloride (OSI-774) Combined with Carboplatin and Paclitaxel Chemotherapy in Advanced Non-Small-Cell Lung Cancer", Journal of Clinical Oncology, Sep. 2005, pp. 5892-5899, vol. 23, No. 25.
Priya Koppikar et al., "Combined Inhibition of c-Src and Epidermal Growth Factor Receptor Abrogates Growth and Invasion of Head and Neck Squamous Cell Carcinoma", Clinical Cancer Research, Jul. 2008, pp. 4284-4291, vol. 14, No. 13.
Niels Reinmuth et al., "Molecular Determinants of Response to RTK-Targeting Agents in Nonsmall Cell Lung Cancer", Int. J. Caner, 2006, pp. 727-734, vol. 119.
Joseph N. Contessa et al., "Inhibition of N-Linked Glycosylation Disrupts Receptor Tyrosine Kinase Signaling in Tumor Cells", Cancer Research, May 2008, pp. 3803-3809, vol. 68, No. 10.
Gerard Crudden et al., "Hpr6 (Heme-1 Domain Protein) Regulates the Susceptibility of Cancer Cells to Chemotherapeutic Drugs", The Journal of Pharmacology and Experimental Therapeutics, 2006, pp. 448-455, vol. 316, No. 1.
Nam-Hee Jung et al., "Evidence for Heme Oxygenase-1 Association with Caveolin-1 and -2 in Mouse Mesangial Cells", IUBMB Life, Sep. 2003, pp. 525-532, vol. 55, No. 9.
Guillermo Garcia-Cardena, "Dissecting the Interaction Between Nitric Oxide Synthase (NOS) and Caveolin", The Journal of Biological Chemistry, Oct. 1997, pp. 25437-25440, vol. 272, No. 41.
S. Difilippantonio et al., "Gene Expression Profiles in Human Non-Small and Small-Cell Lung Cancers", European Journal of Cancer, 2003,pp. 1936-1947, vol. 39.
Julia C. Mallory et al., "Dap1p, A Heme-Binding Protein That Regulates the Cytochrome P450 Protein Erg11p/Cyp51p in Saccharomyces cerevisiae", Molecular and Cellular Biology, Mar. 2005, pp. 1669-1679, vol. 25, No. 5.
Sonia Franco et al., "Effectors of Mammalian Telomere Dysfunction: A Comparative Transcriptome Analysis Using Mouse Models", Carcinogenesis, 2005, pp. 1613-1626, vol. 26, No. 9.
Naoei Yoshitani et al., "A Structure-Based Strategy for Discovery of Small Ligands Binding to Functionally Unknown Proteins: Combination of in Silico Screening and Surface Plasmon Resonance Measurements", Proteomics, 2005, pp. 1472-1480, vol. 5.
Julia C. Mallory et al., "A Novel Group of Genes Regulates Susceptibility to Antineoplastic Drugs in Highly Tumorigenic Breast Cancer Cells", Molecular Pharmacology, 2005, pp. 1747-1756, vol. 68, No. 6.
Randal A. Hand et al., "Hpr6.6 Protein Mediates Cell Death from Oxidative Damage in MCF-7 Human Breast Cancer Cells", Journal of Cellular Biochemistry, 2003, pp. 534-547, vol. 90.
Safety Alerts for Human Medial Products > Tarceva (erlotinib), http://www.fda.gov/Safety/MedWatch/SafetyInformation/SafetyAlertsforHumanMedicalProducts/ucm095059.htm , Sep. 23, 2008, accessed Sep. 16, 2011.
Deborah A. Eppstein et al., "Biological Activity of Liposome-Encapsulated Murine Interferon y is Mediated by a Cell Membrane Receptor", Proc. Natl. Acad. Sci. USA, Jun. 1985, pp. 3688-3692, vol. 82.
Karl J. Hwang et al., "Hepatic Uptake and Degradation of Unilamellar Sphingomyelin/Cholesterol Liposomes: A Kinetic Study", Proc. Natl. Acad. Sci. USA, Jul. 1980, pp. 4030-4034, vol. 77, No. 7.
Deborah K. Armstrong et al., "Epidermal Growth Factor-Mediated Apoptosis of MDA-MB-468, Human Breast Cancer Cells", Cancer Research, Oct. 1994, pp. 5280-5283, vol. 54.
John J. Peluso et al., "Progesterone Receptor Membrane Component-1 (PGRMC1) Is the Mediator of Progesterone's Antiapoptotic Action in Spontaneously Immortalized Granulosa Cells as Revealed by PGRMC1 Small Interfering Ribonucleic Acid Treatment and Functional Analysis of PGRMC1 Mutations", Endocrinology, Feb. 2008, pp. 534-543, vol. 149, No. 2.

(56) References Cited

OTHER PUBLICATIONS

Hugues B. Corbeil et al., "Functional Importance of Complex Formation between the Retinoblastoma Tumor Suppressor Family and Adenovirus E1A Proteins as Determined by Mutational Analysis of E1A Conserved Region 2, Journal of Virology", Oct. 1994, pp. 6697-6709. vol. 68, No. 10.

Peter Sabbatini et al., "Modulation of p53-Mediated Transcriptional Repression and Apoptosis by the Adenovirus E1B 19K Protein, Molecular and Cellular Biology", Feb. 1995, p. 1060-1070, vol. 15, No. 2.

Wilma T. Steegenga et al. "Adenovirus E1A Proteins Inhibit Activation of Transcription by p53, Molecular and Cellular Biology", May 1996, pp. 2101-2109, vol. 16, No. 5.

\* cited by examiner

Pgrmc1   AINGKVFDVTKGRKEYGPEGPYGVFAGRDASRGL-
AtMAPR2  AIKGRVFDVTTGKSFYGSGGDYSMFAGKDASRAL- Pgrmc1   TLSDWESQFTFKYHHVGKLL
AtMAPR2  TLNDWETKFEAKYPVVGRVV

FIG. 7A
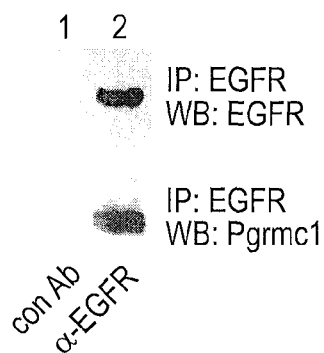
1  2
IP: EGFR
WB: EGFR
IP: EGFR
WB: Pgrmc1
con Ab    α-EGFR
FIG. 7C
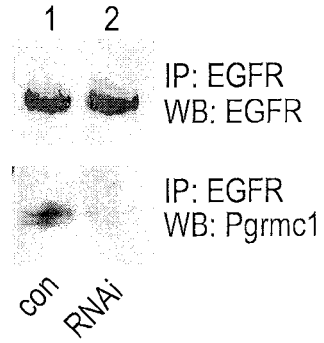
1  2
IP: EGFR
WB: EGFR
IP: EGFR
WB: Pgrmc1
con    RNAi
FIG. 7B
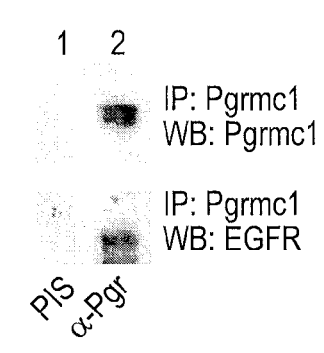
1  2
IP: Pgrmc1
WB: Pgrmc1
IP: Pgrmc1
WB: EGFR
PIS    α-Pgr
FIG. 7D
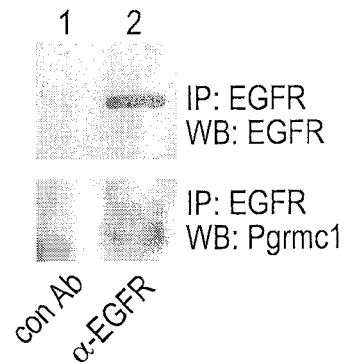
1  2
IP: EGFR
WB: EGFR
IP: EGFR
WB: Pgrmc1
con Ab    α-EGFR
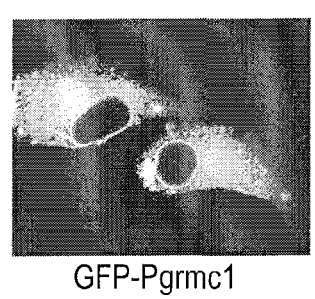
GFP-Pgrmc1
IF: EGFR
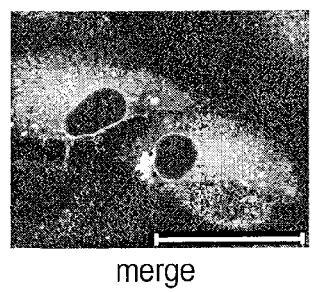
merge
FIG. 7E

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acgagtaaca agctcacgca g                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgcatcatag ttagataaga c                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtggcccacc tggcctcaga c                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatcgcgtct gtggtgctga                                                20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgccaagacg ggaaatgcat c                                              21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgaactgccg agagatgcac                                                20

```
<210> SEQ ID NO 7
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Ile Asn Gly Lys Val Phe Asp Val Thr Lys Gly Arg Lys Phe Tyr
1               5                   10                  15

Gly Pro Glu Gly Pro Tyr Gly Val Phe Ala Gly Arg Asp Ala Ser Arg
            20                  25                  30

Gly Leu Thr Leu Ser Asp Trp Glu Ser Gln Phe Thr Phe Lys Tyr His
        35                  40                  45

His Val Gly Lys Leu Leu
    50

<210> SEQ ID NO 8
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ile Lys Gly Arg Val Phe Asp Val Thr Thr Gly Lys Ser Phe Tyr
1               5                   10                  15

Gly Ser Gly Gly Asp Tyr Ser Met Phe Ala Gly Lys Asp Ala Ser Arg
            20                  25                  30

Ala Leu Thr Leu Asn Asp Trp Glu Thr Lys Phe Glu Ala Lys Tyr Pro
        35                  40                  45

Val Val Gly Arg Val Val
    50
```

AG-205 FOR THE TREATMENT OF BREAST CANCER

SEQUENCE LISTING

The instant application contains a Sequence Listing which has been submitted via EFS-Web and is hereby incorporated by reference in its entirety. Said ACSII copy, created on Jun. 28, 2010, is named 10407260.txt and is 2,846 bytes in size.

TECHNICAL FIELD

Compositions, methods, and combination therapies for the treatment of cancers, including breast, colon, prostate, melanomas, lung cancer, and metastatic disease, are provided. Specifically, compositions comprising small molecule ligands to Pgrmc1 are disclosed for use in treating and inhibiting tumor growth and progression and inhibition of metastases. The compositions and methods using these ligands can be used alone or in combination with other cancer treatment modalities.

BACKGROUND OF THE INVENTION

Cancer is one of the leading causes of death in the United States. The growth and spread of many cancers is driven by genes that are specifically activated in tumors. In many cases, these genes encode proteins involved in metabolism and signaling. Pgrmc1 (progesterone receptor membrane component 1) is a low molecular weight (approximately 25 kDa) protein that was originally thought to be a progesterone receptor. However, it has been demonstrated that Pgrmc1 does not contain any homology to steroid receptors, but instead has homology to cytochrome $b_5$. Pgrmc1 binds to heme and has reducing activity, as the cytochrome proteins do.

Pgrmc1 is over-expressed in multiple types of cancer, including breast, thyroid, colon, ovary and lung cancer. Accordingly, Pgrmc1 has great potential as a biomarker. In breast cancer, Pgrmc1 phosphorylation corresponds with estrogen receptor status, and Pgrmc1 levels correlate with tumor grade in ovarian cancer. Pgrmc1 is also part of a gene signature that predicts hypoxia in breast cancer. Pgrmc1 is also induced during dioxin-induced tumorigenesis and is part of a six gene signature associated with non-genotoxic carcinogens.

These findings are important because they indicate that Pgrmc1 is induced during tumor formation and is up-regulated in tumors in the clinic. One important function of Pgrmc1 in cancer is in chemotherapy resistance. The yeast Pgrmc1 homologue, Dap1 (damage-associated protein), was identified through its role in resistance to chemotherapy. In cancer cells, Pgrmc1 regulates survival in response to chemotherapeutic drugs, both in breast and ovarian cancer cells.

Like cytochrome proteins, Pgrmc1 binds to heme and to P450 proteins, a large class of proteins that are important in drug metabolism, hormone synthesis and metabolism, and lipid synthesis. Pgrmc1 also binds to the cholesterol regulators Insig (insulin-induced gene) and Scap (sterol regulatory element binding protein cleavage activating protein), and to the RNA binding protein PAIR-BP1 (plasminogen activator inhibitor 1 mRNA binding protein), although its biological roles in these interactions is unclear. Indeed, Pgrmc1 does not regulate cholesterol synthesis in cancer cells and has a minimal effect on P450 activity. In contrast, Pgrmc1 has an important role in cell signaling.

Multiple studies have indicated a role for Pgrmc1 in cell signaling. The Pgrmc1 sequence has binding sites for SH2 and SH3 domain-containing proteins and consensus phosphorylation sites for tyrosine kinases. Our laboratory has also shown a more direct role for Pgrmc1 in signaling. When damaged, breast cancer cells suppress death by sustaining signaling through multiple protein kinases, including the serine-threonine kinase Akt, and Pgrmc1 promotes Akt activation. This work was subsequently verified by another group from Germany. Akt is activated by multiple pathways, including the stimulation of receptor tyrosine kinases. This led us to determine the extent to which Pgrmc1 regulates receptor tyrosine kinases in cancer cells, and we have found that Pgrmc1 binds to receptor tyrosine kinases and stabilizes them at the plasma membrane.

Tyrosine kinases span the cell membrane and transmit signals from extracellular polypeptide hormones. Activation of the epidermal growth factor receptor (EGFR) signaling pathway has been linked to increased proliferation, angiogenesis, metastasis and decreased apoptosis (Ritter et al., (2003) *Semin Oncol*, 30:3-11). The earliest studies with EGFR involved an activated form of the receptor expressed from transforming viruses (De Larco et al., (1980) *J Biol Chem*, 255:3685-3690), and EGFR is up-regulated in a variety of tumors, including colorectal cancer (72-82%), head and neck cancer (95-100%), breast cancer (14-91%) and renal cell cancer (59-90% (Saloman et al., (1995) *Crit Rev Oncol Hematol*, 19:183-232). Furthermore, EGFR and HER2/neu over-expression are associated with a poor prognosis in multiple tumor types (Brabender et al., (2001) *Clin Cancer Res.*, 7:1850-1855).

EGFR is inhibited by a growing number of drugs, including the antibody fragments cetuximab, matuzumab, nimotuzumab, zalutumumab and panitumumab and the small molecule inhibitors erlotinib (Tarceva/OSI-774) and gefitinib (Ono et al., (2006) *Clin Cancer Res*, 12:7242-7251; Bareschino et al., (2007) *Ann Oncol*, 18 Suppl 6:vi35-41). EGFR inhibitors have promise for treating cancer, but there effectiveness has been limited clinically. EGFR inhibitors such as erlotinib are effective only in a subset of patients that express mutated forms of the receptor. The most prominent group of patients with these mutations is females that have never smoked, leaving many patients with few therapeutic options. A method of inhibiting the progression of cancers is needed, which utilizes small molecule ligands to Pgrmc1.

SUMMARY OF THE INVENTION

One aspect of the present invention provides a method for inhibiting tumor growth and/or metastatic progression and/or development of metastases comprising administering a ligand to Pgrmc1 to a subject in need thereof in an amount sufficient to inhibit tumor growth and/or metastases. One mechanism of action for the ligand is destabilizing EGFR at the plasma membrane, and other target proteins may apply. The ligand may be AG-205. The tumor may be any tumor, including a solid tumor, such as a breast, colon, lung or prostate cancer, a leukemia, melanoma or a lymphoma. The tumors may be primary lesions or metastatic lesions.

The subject may be administered AG-205 in an amount of about 1 mg/kg subject weight to about 100 mg/kg subject weight. The tumor may be any solid tumor, such as a breast tumor, and the subject may thus be administered AG-205 after surgical excision of the tumor. The subject may be further subjected to surgery, isolated limb perfusion, regional chemotherapy infusion, systemic chemotherapy, or immunotherapy or antisera to treat the tumor.

Regional chemotherapy infusion or the systemic chemotherapy may comprise at least one chemotherapeutic agent selected from the group consisting of: dacarbazine, carmustine, lomustine, tauromustine, fotemustine, semustine, cisplatin, carboplatin, vincristine, vinblastine, vindesine, taxol, dibromodulcitol, detorubicin, doxorubicin, cyclophosphamide, etoposide, piritrexim, and interferon.

The metastases may be a metastasis to brain, lung, liver, peritoneal cavity or bone. The tumor may be further treated with one or more chemotherapeutic agents and/or radiotherapy.

A further aspect of the present invention provides a combination therapy for inhibiting tumor growth and/or metastatic progression and/or development of metastases administering a ligand to Pgrmc1 to a subject in need thereof in an amount sufficient to inhibit tumor growth and/or metastases, wherein the ligand destabilizes EGFR and a chemotherapeutic, and further administering an immunotherapeutic, and/or radiation therapy.

The ligand may be AG-205 or a derivative. The ligand may be administered intravenously, intrathecally, or subcutaneously to a subject in need thereof. AG-205 may be administered in any appropriate amount, for example in amount of about 1 mg/kg subject weight to about 100 mg/kg subject weight. The ligand may be administered daily, weekly, or monthly.

BRIEF DESCRIPTION OF DRAWINGS

FIG. 7 shows that EGFR and Pgrmc1 co-precipitate and co-localize. (A) EGFR was precipitated with the antibody IMC-C225 from serum-starved A549 cells and probed for EGFR (top panel) or Pgrmc1 (second panel). Lane 1 is a control precipitation with an irrelevant antibody. (B) For the inverse experiment, Pgrmc1 was precipitated from A549 cells with pre-immune serum (PIS, lane 1) or an anti-Pgrmc1 antibody (α-Pgr, lane 2). EGFR was detected in the latter reaction (lower panel). (C) EGFR was immuno-precipitated from serum-starved A549/con (lane 1) or A549/RNAi (lane 2) cells. Immuno-precipitation reactions were probed for EGFR (top) or Pgrmc1 (bottom). (D) EGFR was immuno-precipitated with IMC-C225 from MDA-MB-231 breast cancer cells, and precipitation reactions were analyzed by western blot for EGFR (upper panel) or Pgrmc1 (lower panel). (E) The upper panels show fluorescence of Pgrmc1-GFP expressed in A549 cells and immunofluorescence for EGFR, which was detected with a rhodamine-labelled secondary antibody. The lower panel shows a merged image, indicating that Pgrmc1 and EGFR co-localize to an intracellular region adjacent to the nuclear membrane. The bar indicates 25 μm.

DETAILED DESCRIPTION OF THE INVENTION

Figure 1:
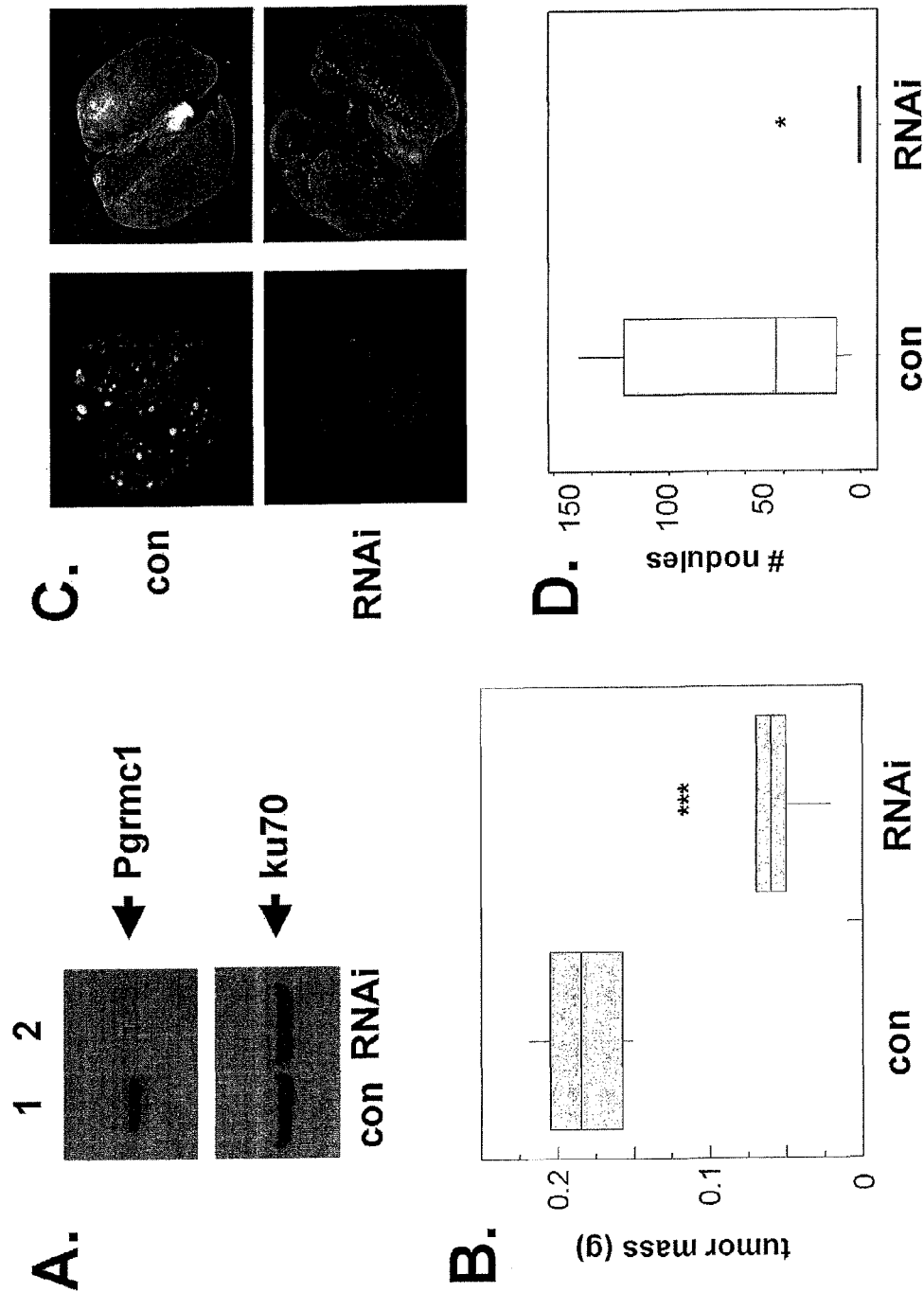
FIG. 1 shows that Pgrmc1 increases tumor growth in mouse xenografts. A549 cells were infected with a lentivirus derived from the pGIPZ plasmid (A549/con) or a lentivirus containing pGIPZ expressing a short hairpin RNA targeting Pgrmc1 (A549/RNAi). Athymic nude mice were injected with A549/con or A549/RNAi cells. (A) Western blot analysis revealed that Pgrmc1 expression was inhibited in the excised A549/RNAi tumors (upper panel, lane 2), while ku70 was unchanged. (B) The excised tumor weight of A549/con was 2.9-fold greater than A549/RNAi. The results support a model in which Pgrmc1 promotes in vivo tumor growth. (C) A549/con cells efficiently colonized the lungs after tail vein injection (upper panels, fluorescent image on left and bright field on right), while A549/RNAi cells were deficient in lung colonization (lower panels). The results from part C were quantitated and are presented graphically in panel D. (For all figures, *=≤0.05; =≤0.01; and *=≤0.005.) These results show that Pgrmc1 increases in vivo tumor growth both as sub-cutaneous tumors and extravasated nodes in the lung.
Figure 2:
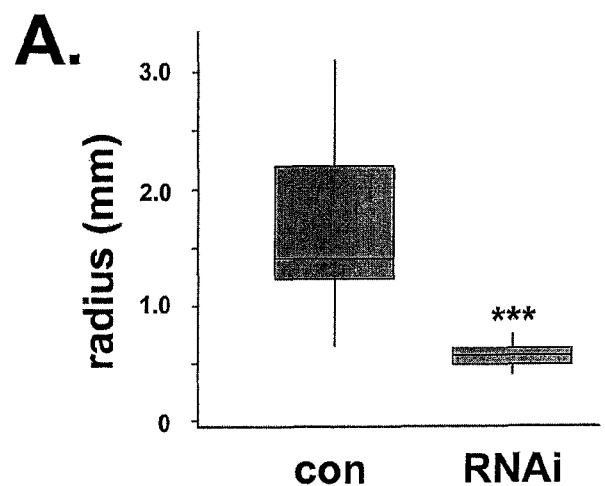
FIG. 2 shows that Pgrmc1 regulates anchorage-independent growth and migration, two key activities of tumor cells. (A) In a soft agar growth assay, which measures anchorage-independent growth, a box plot demonstrates increased colony size in A549/con compared to A549/RNAi cells. Range is indicated by a vertical line, while 95% confidence intervals are indicated by boxes. (B) A549/con cells formed robust colonies in soft agar (left panel), while the colonies arising from A549/RNAi cells were significantly smaller (right panel). In panel C, the migration of A549/con and A549/RNAi cells were measured using the Boyden chamber assay, demonstrating a significant (P=0.002) decrease in migration in the absence of Pgrmc1. Each of the assays was performed in triplicate and is representative of multiple independent experiments.
Figure 2:
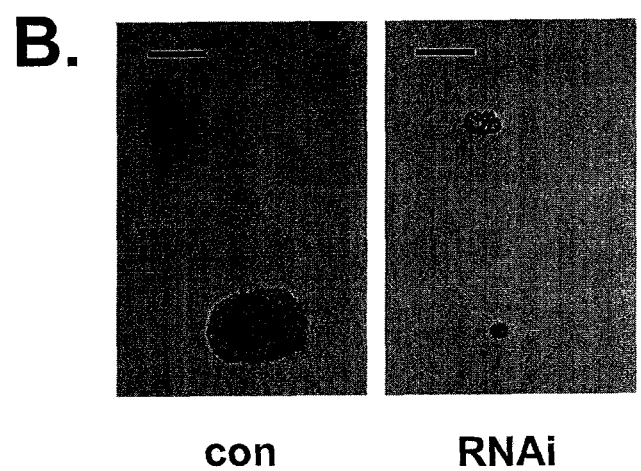
Figure 2:
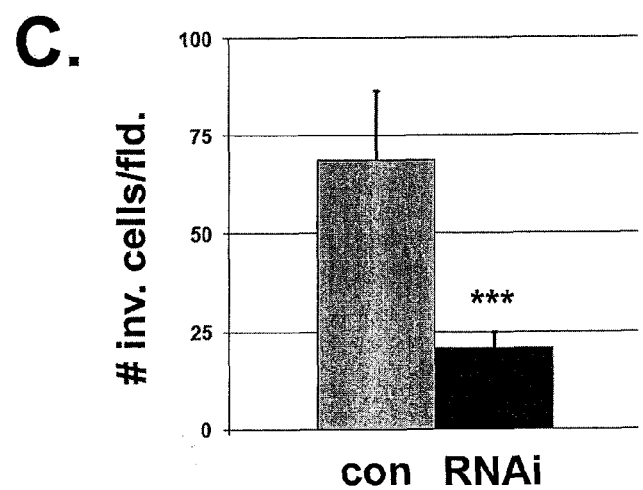
Figure 3:
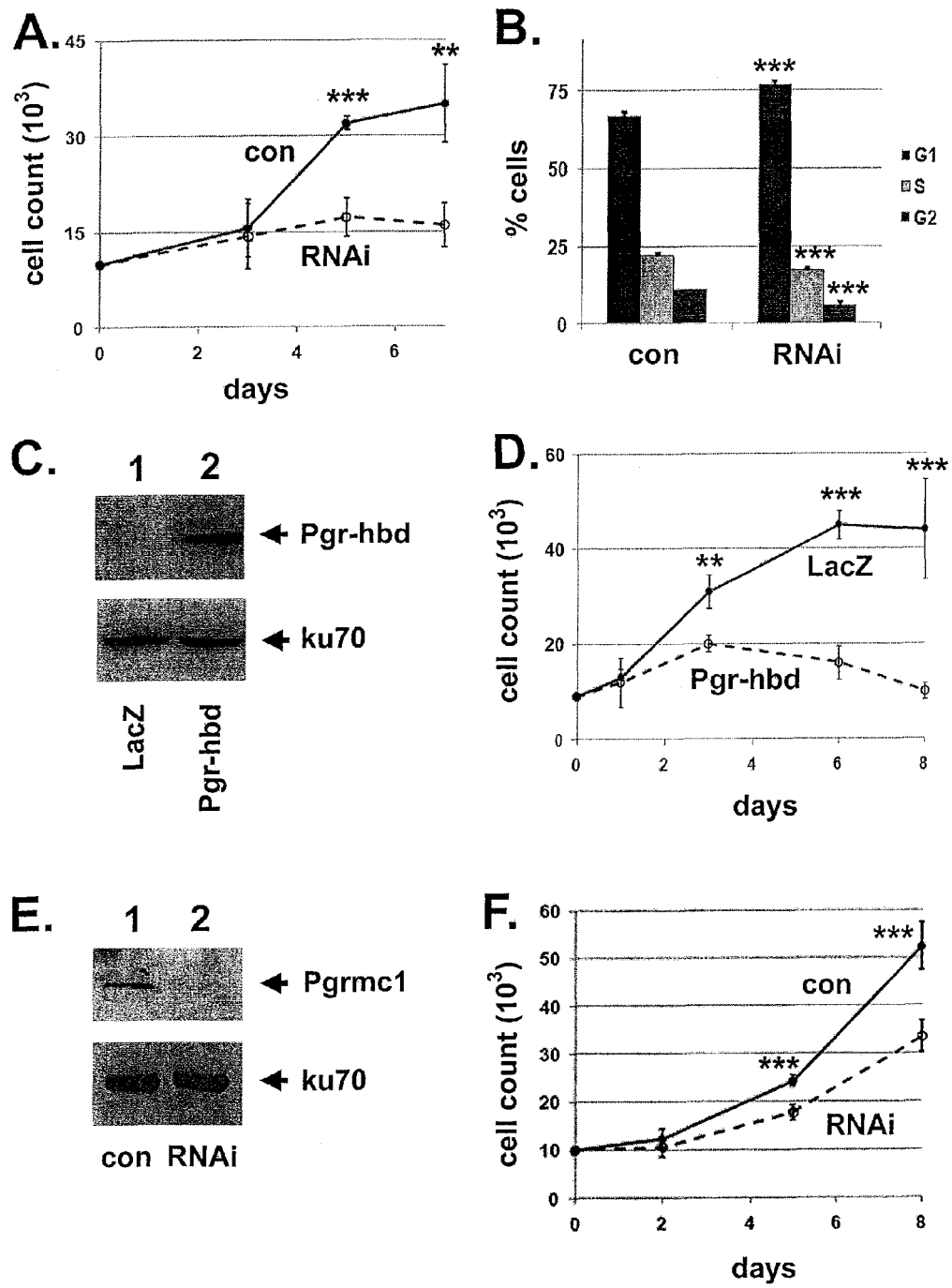
FIG. 3 shows that Pgrmc1 promotes proliferation in the absence of serum in cancer cells. (A) Viability in A549/con and A549/RNAi cells was measured by cell counting from days 1-7 after serum withdrawal. Solid lines represent control cells, while Pgrmc1-inhibited cells are indicated by a dashed line. Measurements were in triplicate, and the results are representative of three separate experiments. (B) The cell cycle profiles A549/con and A549/RNAi cells were analyzed by FACS 24 hours after serum deprivation, and there was a small but significant increase in the $G_1$ population in A549/RNAi cells and a corresponding decrease in S and $G_2$/M populations. (C) Western blot showing the expression of the inactive mutant Pgr-hbd (heme binding-deficient) in cells infected with the Ad-Pgr-hbd adenovirus (lane 2), but not in cells infected with the same dose of control Ad-LacZ adenovirus (lane 1). (D) Viability in Ad-LacZ (solid lines) and Ad-Pgr-hbd-infected cells (dashed lines), measured by cell counting 1-7 days after infection in media lacking serum. (E) Western blot demonstrating Pgrmc1 inhibition by siRNA transfection in MDA-MB-468 cells. (F) Viability of MDA-MB-468 cells transfected with a control siRNA (solid line) or Pgrmc1-targeting siRNA (dashed line). Measurements were in triplicate, and the results are representative of triplicate repeats.
Figures 4A, 4B:
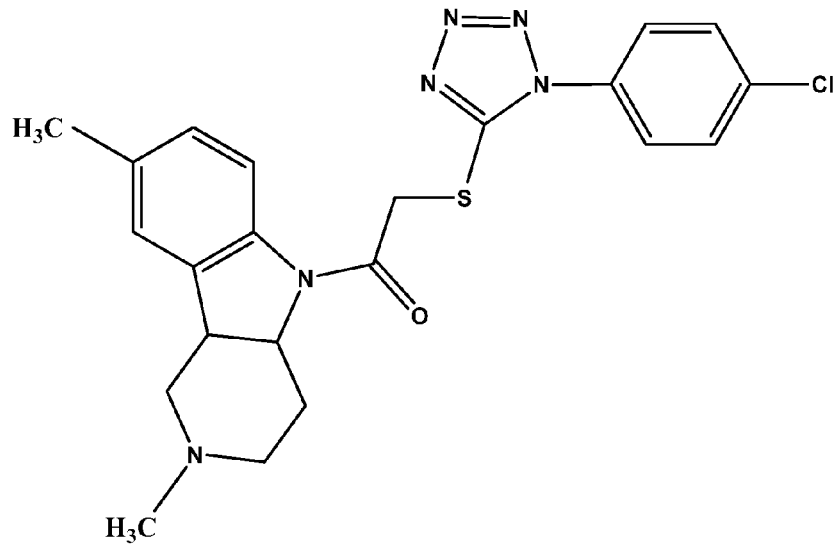
FIG. 4 shows that the AG-205 compound binds to Pgrmc1 and inhibits tumor cell viability. (A) Pgrmc1 (SEQ ID NO: 7) shares homology with AtMAPR2 (SEQ ID NO: 8) (underlined residues), which was the target for a screen for small molecule ligands. The putative heme-binding Tyr106 and Tyr112 are indicated with black boxes. (B) The molecular structure of AG-205 includes multiple aromatic components. (C) Spectroscopic scan of Pgrmc1 with vehicle control compared with vehicle plus 50 □M AG-205. The decrease in relative absorbance at 400 nm is consistent with an AG-205-induced change in the spectral properties of Pgrmc1-heme. The scan is representative of four separate scans using different Pgrmc1 protein preparations. The lower scan is a comparison of purified Pgrmc1 without and with the vehicle control (DMSO). Panels D (A549 cells) and E (MDA-MB-231 cells) are viability assays of cells maintained in 0.1% serum (solid line) or 10% serum (dashed line) and treated with increasing doses of AG-205. Percent viability was determined by cell counting, and "% viability" refers to the cell number relative to the untreated control. The results show a highly significant loss of viability after AG-205 treatment when cells are grown in the absence of serum growth factors.
Figure 4C:
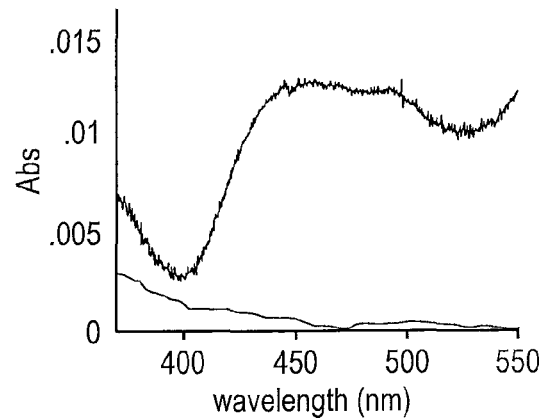
Figure 4D:
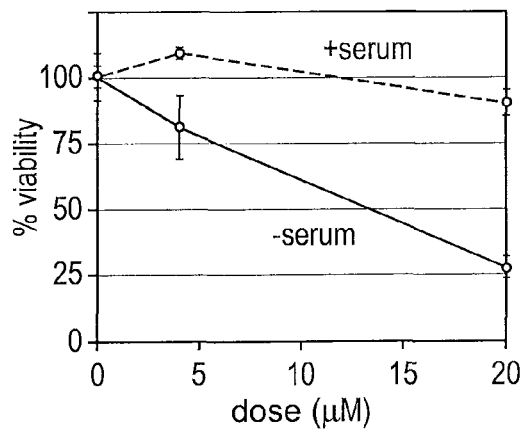
Figure 4E:
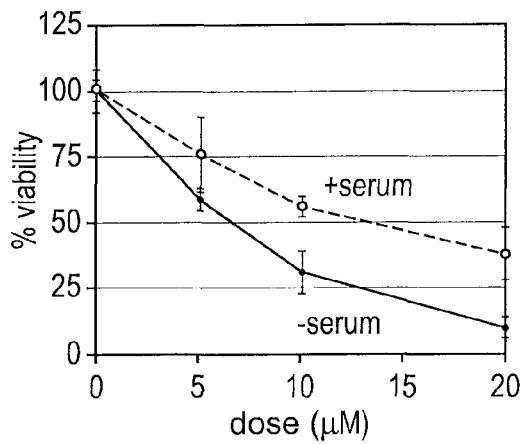
Figure 5A:
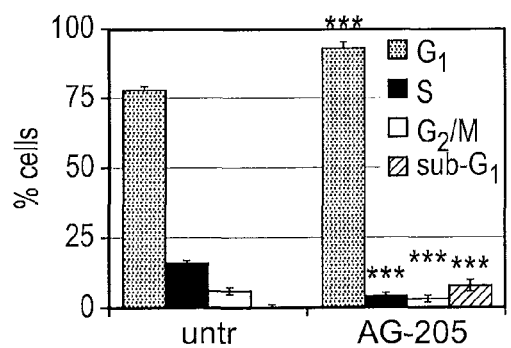
FIG. 5 shows that a Pgrmc1 ligand induces cell cycle arrest in a Pgrmc1-dependent manner. (A) Graph of triplicate FACS analysis. AG-205-treated cells (right columns) had a significant $G_1$ arrest and accumulation of sub-$G_1$ cells, while S and $G_2$/M-phase cells were depleted from the treated population. (B) Protein expression was analyzed by western blot for Pgrmc1 (top) and ku70 (bottom). Cells were treated with 0 (lanes 1), 2 (lanes 2), 10 (lanes 3) or 50 (lanes 4) μM AG-205 for 24 hours. The results show that the Pgrmc1 ligand AG-205 increases Pgrmc1 expression in A549 cells. (C-D) The panels show western blots of phosphorylated ERK1/2 (upper panels) and total ERK1/2 (lower panels) The lanes in panel C are A549/con (lane 1), A549/RNAi (lane 2), A549/LacZ (lane 3) and A549/PGR-hbd cells (lane 4) following 48 hours serum starvation. The cells infected with adenovirus were similar to those described in FIG. 3, panels C and D. In panel D, A549 cells were treated with vehicle (lane 1) or 20 μM AG-205 (lane 2) for 24 hours in serum-free media. (E) A549/con (solid line) or A549/RNAi (dashed line) cells were treated with increasing doses of AG-205 for 72 hours and viability was measured by counting, and "% viability" refers to the cell number relative to the untreated control. (F) Cells expressing LacZ (solid line) or the Pgrmc1-hbd heme binding-deficient mutant (dashed line), were treated with increasing doses of AG-205. The Pgrmc1 inhibitor partially reversed the loss of viability characteristic of Pgrmc1-hbd-expressing cells. Percent viability was determined by cell counting, and "% viability" refers to the cell number relative to the untreated control. For each experiment, the results are representative of experiments performed at least in duplicate.
Figure 5B:
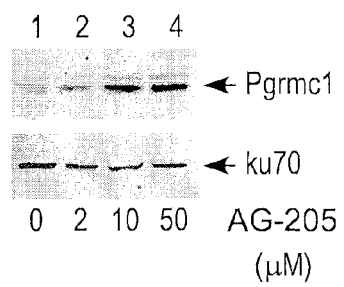
Figure 5C:
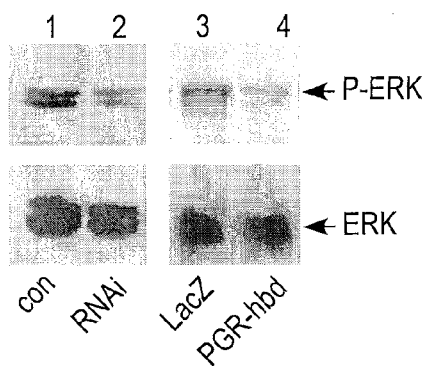
Figure 5D:
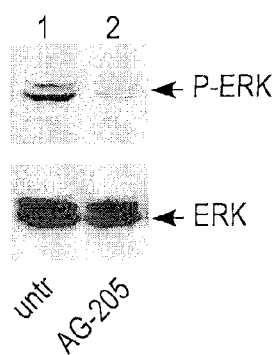
Figure 5E:
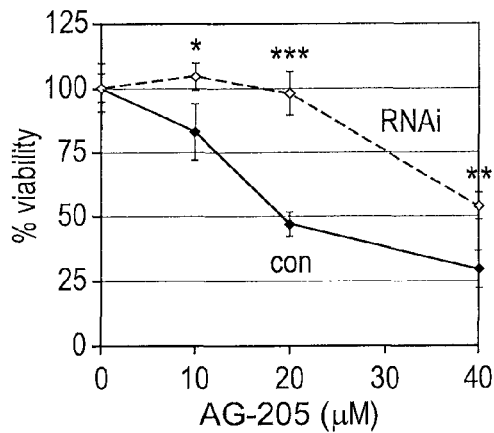
Figure 5F:
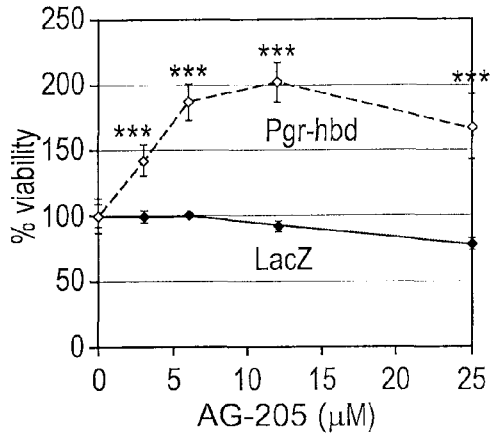
Figure 6:
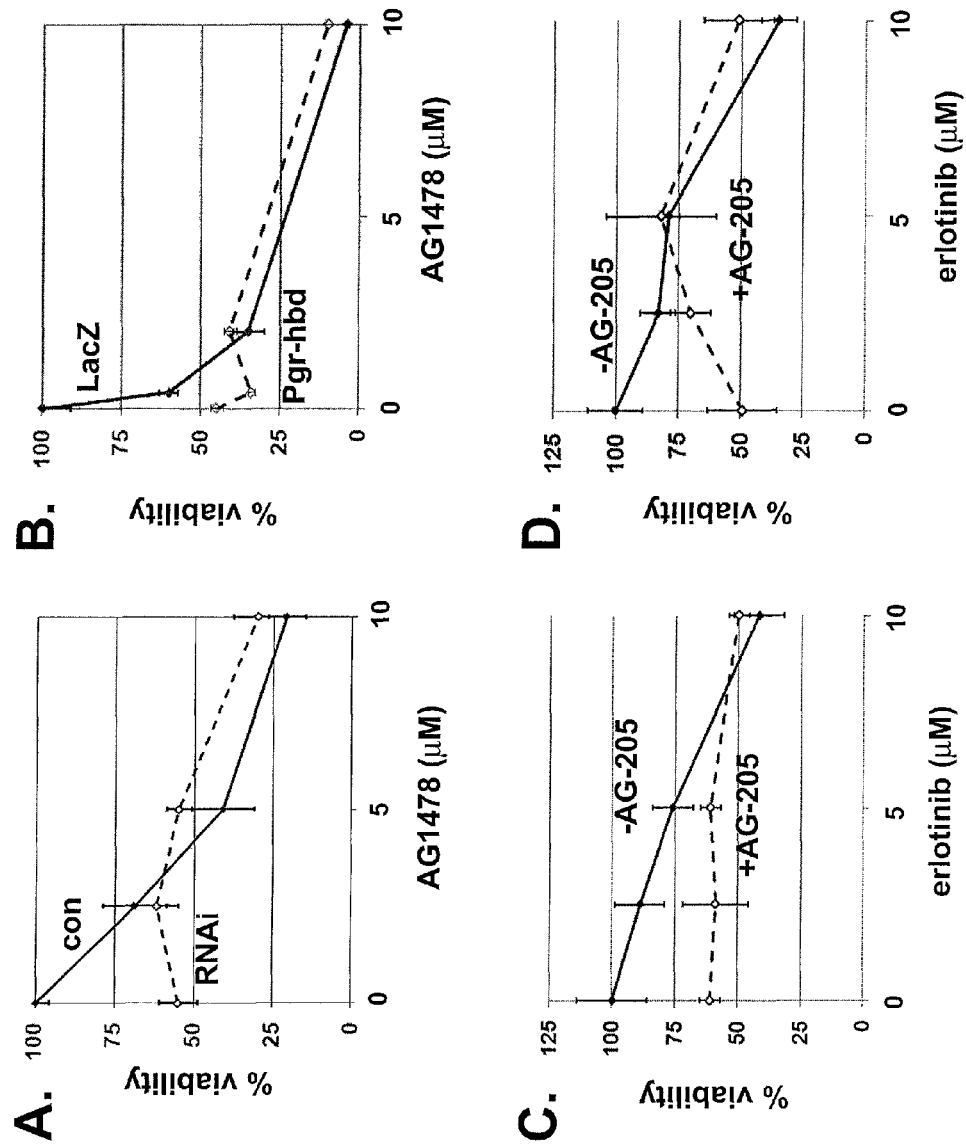
FIG. 6 shows that Pgrmc1 promotes EGFR inhibitor sensitivity. (A) A549/con (solid line) or A549/RNAi (dashed line) cells were maintained in media lacking serum and treated with 2.5-10 μM of the EGFR inhibitor AG1478 for 96 hours. Percent viability was determined by cell counting, and for all of the panels "% viability" refers to the cell density relative to untreated cells. (B) AG1478 susceptibility in Ad-LacZ and Ad-Pgr-hbd-infected A549 cells, measured by MTT assay 4 days after infection in serum-free media containing increasing doses of AG-1478. Solid lines represent cells infected with the control Ad-LacZ, while Ad-Pgr-hbd-infected cells are indicated by a dashed line. (C) A549 cells were treated with vehicle (solid line) or 10 μM AG-205 (dashed line) plus increasing doses of erlotinib and counted. (D) MDA-MB-231 breast cancer cells were treated with AG-205 and erlotinib as described in panel C. Each of the experiments is representative of experiments performed at least in triplicate. The results indicate that increases in proliferation in Pgrmc1-expressing cells are reversed by EGFR inhibitors.
Figure 8:
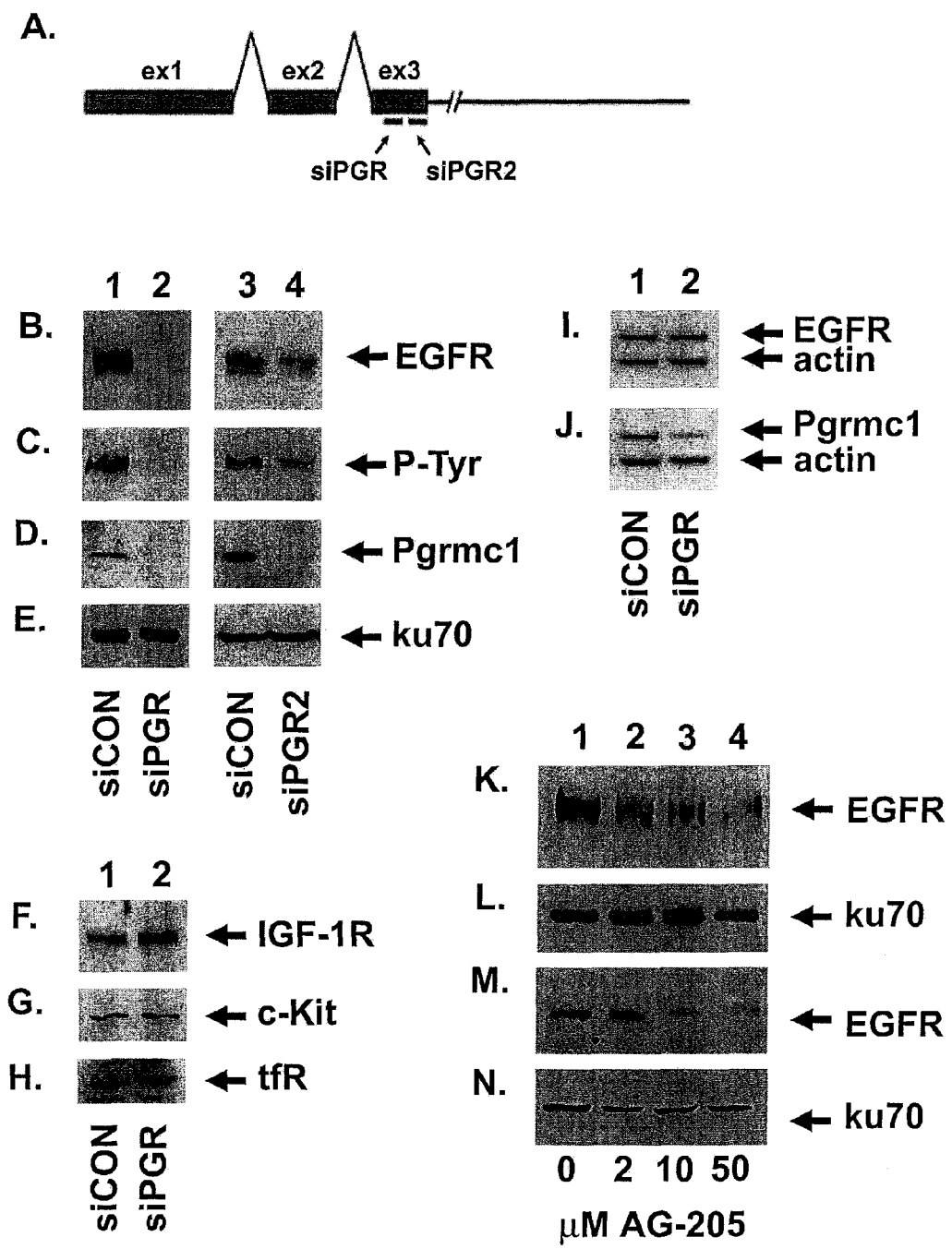
FIG. 8 shows that Pgrmc1 increases EGFR levels in MDA-MB-468 breast cancer cells. Panel A is a diagram indicating the positions of the siRNA molecules targeting Pgrmc1. Exons 1, 2 and 3 are indicated by "ex". MDA-MB-468 cells were transfected with a control siRNA (siCON, lanes 1 and 3) or two separate siRNAs targeting Pgrmc1 (siPGR and siPGR2, lanes 2 and 4, respectively). In panels B-E and H-L, protein levels were analyzed by western blot for EGFR (B), phospho-tyrosine (C), Pgrmc1 (D) and ku70 (E), as a control for protein loading. Panels F—H show western blot analyses for (F) IGF-1R, (G) c-Kit and (H) tfR. In panels I and J, transcript levels were analyzed by reverse transcriptase-PCR for EGFR (I) and Pgrmc1 (J). The top band indicates the gene of interest, while actin primers were included in the same reaction as a control for cDNA loading. The results show that Pgrmc1 regulates EGFR protein levels with little effect on EGFR transcription. In panels K-L, MDA-MB-468 cells were treated with increasing doses of the Pgrmc1 ligand AG-205. Protein expression was analyzed by western blot for EGFR (K) and ku70 (L). Cells were treated with 0 (lanes 1), 2 (lanes 2), 10 (lanes 3) or 50 (lanes 4) μM AG-205 for 24 hours in serum-free medium. In panels M-N, A549 cells were treated with the same doses and analyzed for EGFR (M) and ku70 (N). The results show that the Pgrmc1 ligand AG-205 decreases EGFR protein levels. Expression analyses were repeated at least in duplicate throughout.

As used throughout the specification and the appended claims, the terms listed below have the following meanings, wherein "a" means one or more:

By "EGFR" is meant epidermal growth factor receptor.

By "RTK" is meant receptor tyrosine kinase.

By "Pgrmc1" is meant progesterone receptor membrane component 1.

By the term "subject" or "patient" as used herein is meant to include a mammal. The mammal can be a canine, feline, primate, bovine, ovine, porcine, camelid, caprine, rodent, or equine. Preferably the mammal is human.

The term "efficacy" as used herein refers to the effectiveness of a particular treatment regime. Efficacy can be measured based on such characteristics (but not limited to these) as inhibition of tumor growth, reduction of tumor mass, reduction of metastatic lesions as assessed, for example, by radiologic imaging, slowed tumor growth, lack of detectable tumor associated antigens, and the like. Additional methods of assessing tumor progression are discussed herein and would be known to the treating and diagnosing physicians.

By the phrases "pharmaceutically acceptable carrier" and "pharmaceutically acceptable excipient" are intended to mean any compound(s) used in forming a part of the formulation that is intended to act merely as a carrier, i.e., not intended to have biological activity itself. The pharmaceutically acceptable carrier or excipient is generally safe, non-toxic, and neither biologically nor otherwise undesirable. A pharmaceutically acceptable carrier or excipient as used herein includes both one and more than one such carrier or excipient.

The terms "treating", and "treatment", and the like are used herein to generally mean obtaining a desired pharmacological and physiological effect. More specifically, the reagents described herein which are used to treat a subject with a tumor and metastatic disease generally are provided in a therapeutically effective amount to achieve any one or more of the following: inhibited tumor growth, reduction in tumor mass, loss of metastatic lesions, inhibited development of new metastatic lesions after treatment has started, or reduction in tumor such that there is no detectable disease (as assessed by e.g., radiologic imaging, biological fluid analysis, cytogenetics, fluorescence in situ hybridization, immunocytochemistry, colony assays, multiparameter flow cytometry, or polymerase chain reaction). The term "treatment", as used herein, covers any treatment of a disease in a mammal, particularly a human.

By "therapeutically effective amount" is meant an amount of an agent, reagent, compound, composition, or combination of reagents disclosed herein that when administered to a mammal is sufficient to be effective against the tumor.

By the term "tumor" is meant to include both benign and malignant growths or cancer. Thus, the term "cancer", unless otherwise stated, can include both benign and malignant growths. Preferably, the tumor is malignant. The tumor can be a solid tissue tumor such as a melanoma, or a soft tissue tumor such as a lymphoma, a leukemia, or a bone cancer.

By the term "primary tumor" is meant the original neoplasm and not a metastatic lesion located in another tissue or organ in the patient's body.

By the terms "metastatic disease", "metastases", and "metastatic lesion" are meant a group of cells which have migrated to a site distant relative to the primary tumor.

Receptor tyrosine kinases were among the first proto-oncogenes ever identified. Alterations in RTKs, such as EGFR and HER2/neu, are associated with a variety of cancers. RTK inhibitors such as herceptin, erlotinib and iressa are currently among the most promising agents in development for treating cancer, and they extend both overall survival and disease-free progression in some patients. RTK inhibitor treatments do not have the harsh side effects associated with traditional chemotherapy. However, patients do not respond uniformly to these RTK inhibitors, and comprehensive genetic screening of every cancer patient will likely be expensive and complex.

Pgrmc1 (progesterone receptor membrane component 1) is a protein that is up-regulated in multiple types of cancer, including breast, lung, colon and ovarian cancer. Pgrmc1 binds to heme and stimulates the activity of P450 proteins, which catalyze many critical reactions in lipid and hormone synthesis. It has been previously shown that Pgrmc1 regulates protein kinase signaling downstream from EGFR, and the role of Pgrmc1 in activating EGFR has been investigated. Pgrmc1 was inhibited in A549 human lung cancer cells and MDA-MB-468 human breast cancer cells by a combination of siRNA and shRNA expression directed from a lentivirus. Pgrmc1 inhibition caused a 4-25-fold decrease in EGFR levels. This drop in EGFR was accompanied by a 27-40% decrease in proliferation in MDA-MB-468 and A549 cells. Pgrmc1 also caused a 2.9-fold drop in anchorage-independent growth and 4.1-fold inhibited migration in A549 cells. In both cell types, Pgrmc1 inhibition had no effect on EGFR transcription, indicating that the effect was post-translational. Pgrmc1 bound to caveolin, a membrane protein that binds to cholesterol and receptor tyrosine kinases. Finally, a Pgrmc1 ligand de-stabilized EGFR and induced cell death in multiple tumor cell lines.

Pgrmc1 is a component of a hormone/drug receptor complex that is over-expressed in tumors and stabilizes RTKs. Furthermore, new Pgrmc1 inhibitors de-stabilize EGFR through a distinct mechanism from other agents and could be used in combinations with multiple existing drugs. This could provide a new therapeutic option in the clinic for cancer patients that have developed resistance to currently available drugs.

It has been found that Pgrmc1 directly associates with EGFR in lung and breast cancer cells, as well as in cells of other cancer types. Inhibition of Pgrmc1 causes EGFR levels to diminish at the plasma membrane, likely due to defective trafficking to the plasma membrane or increased endocytosis from the plasma membrane. By stabilizing EGFR at the plasma membrane, Pgrmc1 increases the sensitivity of lung cancer cells to the EGFR inhibitor erlotinib, underscoring the importance of Pgrmc1 in EGFR function. Furthermore, genetic inhibition of Pgrmc1 de-stabilizes EGFR in breast cancer cells expressing high levels of EGFR, suggesting multiple routes through which Pgrmc1 affects EGFR function.

The small molecule ligand of Pgrmc1, called AG-205, was identified in 2005 using an in silico screen with the Pgrmc1 homologue from the flowering plant *Arabidopsis thaliana*. AG-205 was found to bind to At Pgrmc1, but no subsequent research was conducted on the biochemical or biological activity of AG-205. It was found that AG-205 is toxic to multiple cancer cell lines from lung, breast, colon and prostate tissues. Any cell line over-expressing Pgrmc1 may be targeted by AG-205, due to the role of Pgrmc1 in promoting cell signaling. Indeed, AG-205 is most active when serum is absent, likely because cells are deprived of super-physiological levels of growth factors and require Pgrmc1 for efficient survival signaling. AG-205 may be limited by its solubility, and thus derivatives of AG-205 are included herein, as optimized for their enhanced solubility, specificity and delivery.

Receptor Tyrosine Kinases as Cancer Therapeutic Targets

Receptor tyrosine kinases (RTKs) were originally discovered through their association with cancer. EGFR has been identified as regulating RTK stability and activation.

EGFR (Erb-B1) is part of a family of proteins that includes Erb-B2/HER2/neu, Erb-B3/HER3 and ErbB4/HER4. Activation of the EGFR signaling pathway has been linked to increased proliferation, angiogenesis, metastasis and decreased apoptosis (Ritter et al., (2003) *Semin Oncol* 30(1 Suppl 1):3-11). At least five mitogenic growth factors bind and activate EGFR: EGF, TGF-α, amphiregulin, heparin-binding EGF and epiregulin. The earliest studies with EGFR involved an activated form of the receptor expressed from transforming viruses (De Larco et al., (1980) *The Journal of Biological Chemistry* 255(8):3685-3690; Downward et al., (1984) *Nature* 307(5951):521-527), and c-EGFR and HER2/neu can transform NIH-3T3 cells (Di Fiore et al. (1987) *Cell* 51(6):1063-1070). EGFR is up-regulated in a variety of tumors, including colorectal cancer (72-82%), head and neck cancer (95-100%), breast cancer (14-91%) and renal cell cancer [59-90% (Salomon et al., (1995) *Crit Rev Oncol Hematol* 19(3):183-232)]. Furthermore, EGFR and HER2/neu over-expression are associated with a poor prognosis in multiple tumor types [(Brabender et al., (2001) *Clin Cancer Res* 7(7):1850-1855), reviewed in (Ono et al., (2006) *Clin Cancer Res* 12(24):7242-7251)]. EGFR is activated by a number of mechanisms, including over-expression, amplification and activating mutations Sebastian et al., (2006) *Biochim Biophys Acta* 1766(1):120-139).

EGFR is inhibited by the drug erlotinib (Tarceva/OSI-774), a quinazoline-based agent which associates with the ATP binding region of EGFR (Bareschino et al., (2007) *Ann Oncol* 18 Suppl 6:vi35-41). Erlotinib was approved by the FDA in 2004 for the treatment of chemotherapy-resistant advanced NSCLC following a 731 patient multicenter phase III trial in which erlotinib significantly improved overall survival and progression-free survival in NSCLC patients after one or two chemotherapy regimens had failed.

One promising strategy with EGFR inhibitors appeared to be combining them with other drugs. However, clinical trials combining EGFR inhibitors with chemotherapy have not yet been successful (Herbst et al., (2005) *J Clin Oncol* 23(25): 5892-5899). EGFR and Src inhibitors are a promising combination for head and neck cancer (Koppikar et al., (2008) *Clin Cancer Res* 14(13):4284-4291). Thus, erlotinib and other targeted therapeutics have promise for treating cancer, but in clinical terms, the responses are far from complete. One approach to more effective targeting of these inhibitors is to design drug combinations that accommodate the regulation and trafficking of EGFR in lung cancer cells.

Another strategy is to identify patients with the greatest potential of benefiting from EGFR inhibitors. Cell lines exhibit markedly different responses to EGFR inhibitors (Ono et al., (2006) *Clin Cancer Res* 12(24):7242-7251), a fact that probably reflects the cells' genetic backgrounds. Where EGFR performs an essential function in proliferation and survival, the drugs are highly effective. In other backgrounds, the benefits of the drugs are limited. Responsiveness to EGFR inhibitors is difficult to predict. Tumors harboring EGFR activating mutations respond well to EGFR inhibitors, but some tumors expressing mutant EGFR are inhibitor-resistant (Reinmuth et al., (2006) *Int J Cancer* 119(4):727-734). In addition, some tumors with amplified EGFR have increased sensitivity to EGFR inhibitors.

Recently, there has been increasing interest in blocking RTK function by inhibiting their processing, and inhibitors of glycosylation and chaperones are effective at disrupting RTK function and drug resistance (Contessa et al., (2008) *Cancer Res* 68(10):3803-3809).

Pgrmc1 (progesterone receptor membrane component 1) is a member of a multi-protein progesterone-binding complex (Meyer et al., (1996) *Eur J Biochem* 239(3):726-731), and Pgrmc1 has also been named Hpr6.6 [human membrane progesterone receptor (Gerdes et al., (1998) *Biol Chem* 379(7):907-911)]. Pgrmc1 does not bind directly to progesterone (Min et al., (2005) *Febs J* 272(22):5832-5843) and has no homology with steroid receptors (Mifsuf et al., (2002) *Genome Biol* 3(12):RESEARCH0068), nuclear or membrane-associated. Instead, Pgrmc1 resides in the endoplasmic reticulum (Crudden et al., (2005) *Tumour Biol* 26(3):142-146), where it binds to various proteins implicated in lipid metabolism, including caveolin/Cav1, Insig-1 (insulin-induced gene), Scap (SREBP cleavage activating protein) and P450 proteins (Bramley et al., (2002) *Domest Anim Endocrinol* 23(1-2):3-12). These findings suggest a model in which a multi-protein Pgrmc1 complex responds to changes in lipid and/or hormone levels and transports signaling proteins to the cell membrane.

The endogenous Pgrmc1 ligand is heme (Crudden et al. (2006) *J Pharmacol Exp Ther* 316(1):448-455). Pgrmc1 shares key structural motifs with cytochrome $b_5$ (Mifsud 2002), a heme binding protein that activates cytochrome P450 proteins *Pharmacology & therapeutics* 97(2):139-152). Pgrmc1 binds and activates P450 proteins (Hughes et al., (2007) *Cell Metab* 5(2):143-149), which metabolize drugs, hormones and lipids. Heme is also implicated in Cav1 function, because Cav1 binds to several heme-containing proteins, including heme oxygenase (Jung et al., (2003) *IUBMB Life* 55(9):525-532) and NOS (Garcia-Cardena et al., (1997) *The Journal of biological chemistry* 272(41): 25437-2544).

The heme binding site of Pgrmc1 is predicted to be a prominent groove at the center of the protein. Notably, all of the residues that are known to be important in heme binding cluster along one face of the protein. The Asp120 residue, which is required for heme binding (Crudden et al., 2006), is at the center of the groove. The Tyr107 and Tyr113 sites are required for heme binding and localize to the right of the groove. Interestingly, the Tyr113 site is a proposed phosphorylation site for the Abl tyrosine kinase (Cahill (2007) *J Steroid Biochem Mol Biol* 105(1-5):16-36), but this phosphorylation event has not been formally demonstrated. Finally, the Tyr164 residue, which is analogous to the Tyr138 of yeast, is required for heme binding and localizes to the side of the heme-binding groove.

It has been shown that Pgrmc1 stabilizes EGFR in human cancer cells. This follows on earlier findings that Pgrmc1 is over-expressed in breast tumors and in cancer cell lines from the colon, thyroid, lung, and cervix (Crudden et al., (2005) *Tumour Biol* 26(3):142-146). In ovarian cancer, Pgrmc1 expression increased in advanced stage tumors, and Pgrmc1 was homogeneously expressed within the tumors (Peluso et al., (2008) *J Clin Endocrinol Metab* 93(5):1592-1599). Microarray analyses have also detected Pgrmc1 expression in colon, lung, ovarian and breast tumors (Difilippantonio et al., (2003) *Eur J Cancer* 39(13):1936-1947).

Yeast cells lacking the Pgrmc1 homologue, Dap1, are sensitive to DNA damage (Craven et al., (2007) *J Biol Chem* 282(50):36543-36551) due to a failure in a repair process. Like Pgrmc1, Dap1 binds to heme (Ghosh et al., (2005) *Biochemistry* 44(50):16729-16736), and heme binding is essential for damage resistance (Mallory et al., (2005) *Mol Cell Biol* 25(5):1669-1679). Furthermore, exogenous heme or over-expression of the heme synthetic pathway can overcome the requirement for Dap1 in damage resistance *J Biol Chem* 282(50):36543-36551).

Because of the role of Dap1 in damage resistance, whether Pgrmc1 has an analogous function in cancer cells was tested. Pgrmc1 was inhibited by expression of a dominant-negative, heme binding-deficient mutant or by siRNA, and either treatment sensitized breast cancer cells to the chemotherapeutic drugs doxorubicin and camptothecin (Crudden et al., (2006) *J Pharmacol Exp Ther* 316(1):448-455). These drugs are inhibitors of topoisomerase II and topoisomerase I, respectively. Peluso, et al. reported similar results in ovarian cancer cells treated with cisplatin (Peluso et al., 2008). Pgrmc1 expression is induced by chemotherapy (Crudden et al., 2006) and in mouse cells with short telomeres (Franco et al., (2005) *Carcinogenesis* 26(9):1613-1626), which suffer chromosomal damage during senescence and crisis. These results suggest that Pgrmc1 induction is a consequence of DNA damage, and Pgrmc1 plays a role in suppressing damage-induced cell death in cancer cells.

Ligands for the Pgrmc1 Heme Binding Site

Pgrmc1 is unusual because it has both the characteristics of a cytochrome and a receptor, suggesting a regulatory point in metabolism. Yoshitani, et al. identified a novel class of Pgrmc1 ligands by combining molecular modeling of the *Arabidopsis thaliana* Pgrmc1 structure with binding assays using Pgrmc1 immobilized on a Biocore chip ((2005) *Proteomics* 5(6):1472-1480). *A. thaliana* is structurally conserved with mammalian Pgrmc1 in the heme-binding site, and the two proteins have a similar overall structure. While Yoshitani identified four Pgrmc1 ligands and measured their binding affinity, they performed only biochemical assays and did not explore a physiological function for the ligands.

Pgrmc1 ligands are predicted to bind to the heme-binding crevice of Pgrmc1 (Yoshitani et al., (2005) *Proteomics* 5(6):1472-1480), suggesting that the ligands could displace heme from its binding site. Heme binding is critical for the activity of Pgrmc1 homologues (Hughes et al., (2007) *Cell Metab* 5(2):143-149), suggesting that the Pgrmc1 ligands would act as Pgrmc1 inhibitors. The present invention provides a mechanism showing that these ligands inhibit EGFR stability and induce cell death in cancer cells.

Receptor tyrosine kinases are among the most important proteins in cancer, driving the growth, survival and spread of tumor cells. A previously unknown step in RTK regulation has been identified, in which a heme-binding steroid receptor component, Pgrmc1, stabilizes EGFR and promotes proliferation, anchorage-independent growth and invasion. It has previously been shown that Pgrmc1 is over-expressed in tumors (Crudden et al. (2005) *Tumour Biol* 26:142-6), including breast tumors. Pgrmc1 is induced by chemotherapy (Mallory et al., (2005) *Mol Pharmacol* 68:1747-56) and is implicated in chemotherapy resistance (Crudden et al., (2006) *J Pharmacol Exp Ther* 316:448-55). However, many tumors express Pgrmc1 prior to chemotherapy, suggesting a function for Pgrmc1 other than drug resistance. In fact, Pgrmc1 activates Akt (Hand et al. (2003) *J Cell Biochem* 90:534-47), a pro-survival signaling kinase, in breast cancer cells. A novel Pgrmc1 ligand has been identified that de-stabilizes EGFR and triggers cell death.

Another potential mechanism through which Pgrmc1 might stabilize EGFR is via an interaction with the PAIR-BP1 mRNA binding protein. The target of PAIR-BP1 is the PAI1 protein, which is associated with tumor invasion and vascularization (Bajou et al. (1998) *Nat Med* 4:923-8). However, in Pgrmc1-inhibited cells, no change in PAI1 transcript levels was detected. This result does not support a model in which Pgrmc1 stabilizes EGFR by altering PAI1 levels via binding to PAIR-BP1. However, the model that a Pgrmc1-PAIR-BP1 complex stabilizes EGFR via an intermediate other than PAI1 cannot be excluded.

Because the predicted structure of Pgrmc1 contains a well-defined ligand binding domain (Song et al., (2004) *J Biomol NMR* 30:215-8), the ability of a novel Pgrmc1 ligand to inhibit Pgrmc1 was tested. AG-205 inhibited EGFR stability at micromolar levels, similar to the effect of Pgrmc1 inhibition by RNAi, and AG-205 induced cell death in cancer cells. This is surprising, because siRNA for Pgrmc1 was not toxic. This suggests that other proteins related to Pgrmc1, including Pgrmc2 (Gerdes et al. (1998) *Biol Chem* 379:907-11) and Neudesin/SPUF (Kimura et al., (2008) *J Biol Chem* 283:4323-31), may compensate for the loss of Pgrmc1 following siRNA inhibition. Because these proteins have a similar heme-binding domain to Pgrmc1, they likely bind to AG-205. Alternately, AG-205 may bind to proteins other than Pgrmc1 that are important in maintaining viability in cancer cells.

The effect of a Pgrmc1 ligand on EGFR levels and viability was also tested. The AG-205 compound was identified by Yoshitani, et al. ((2005) *Proteomics* 5(6):1472-1480), who used a two-step process that began with computational screening based on the NMR structure of an *A. thaliana* Pgrmc1 homologue, called AtMAPR2 (*A. thaliana* membrane-associated progesterone receptor 2) or At2g24940. Pgrmc1 contains 64% identity with AtMAPR2 in two separate regions of the heme-binding domain, beginning with residues Ala90 and Thr151. The screen for AtMAPR2 ligands began with modeling of the putative heme-binding site of AtMAPR2. From the computational screen, 69 compounds were selected for further testing with purified AtMAPR2 using surface plasmon resonance. The affinity characteristics of the top four candidates were then tested individually. All of the four highest affinity ligands had a similar structure, with aryl rings bridged by a short backbone.

There are four aromatic ligands for the *Arabidopsis thaliana* Pgrmc1 homologue, AtMAPR2, which is highly conserved with human Pgrmc1 in the heme-1 domain. One of the AtMAPR2 ligands with the highest binding affinity is called AG-205 and is an aromatic compound. Based on the putative structure of Pgrmc1, the majority of the conserved residues cluster in a pocket that is analogous to the AtMAPR2 ligand binding site. Tyr106 and Tyr112 are required for heme binding. The addition of AG-205 to purified Pgrmc1 caused a shift in absorbance at approximately 400 nm, with a smaller shift at approximately 530 nm. The results suggest that AG-205 alters the spectroscopic properties of the Pgrmc1-heme complex.

EGFR is one of the most prominent therapeutic targets in cancer, and is inhibited clinically by the antibody fragment erbitux/cetuximab and by the small molecule inhibitors erlotinib and gefitinib. However, the fraction of patients that responds to erlotinib is somewhat limited, and there are safety concerns with erlotinib as well (see the Food and Drug Administration website Medwatch for Tarceva (www.fda.gov/medwatch/safety/2008/safety08.htm#Tarceva)).

One of the curious features of AG-205 is that it is more active against cell lines expressing wild-type EGFR than the $\Delta$E746-A750 mutant EGFR. In contrast, the $\Delta$E746-A750 mutant is more sensitive to erlotinib than cells expressing wild-type EGFR. Furukawa, et al. have shown that $\Delta$E746-A750 mutant EGFR in constitutively active and exhibits deficient Cbl binding, ubiquitination and endocytosis (Furukawa et al., (2007) *DNA Cell Biol* 26:178-85). Interestingly, it was found that there is an intracellular pool of EGFR in the early stages following AG-205 treatment in MDA-MB-468 cells. Thus, one possible model is that Pgrmc1 sustains EGFR at the cell membrane, and that $\Delta$E746-A750 mutants do not require Pgrmc1 for their membrane localization.

In one aspect of the invention, the methods and compositions disclosed herein can be used to treat, inhibit or slow the progression of malignancies. These malignancies can be solid or soft tissue tumors. Soft tissue tumors, or liquid tumors, include bone cancers, lymphomas, and leukemias. Another aspect of the invention is to use the methods and compositions to inhibit or prevent metastases or metastatic progression.

Thus, an aspect of the invention is to treat tumors or metastatic disease with a ligand to Pgrmc1. These ligands can be used alone, in combination with each other, or in combination with other cancer modalities, such as but not limited to chemotherapy, surgery, radiotherapy, hyperthermia, immunotherapy, hormone therapy, biologic therapy (e.g., immune effector mechanisms resulting in cell destruction, cytokines, immunotherapy, interferons, interleukin-2, cancer vaccine therapy, and adoptive therapy), and drugs to ameliorate the adverse side effects of such cancer modalities.

The term cancer embraces a collection of malignancies with each cancer of each organ consisting of numerous subsets. Typically, at the time of cancer diagnosis, "the cancer" consists in fact of multiple subpopulations of cells with diverse genetic, biochemical, immunologic, and biologic characteristics.

Preferred cancers to be treated by the present invention include but are not limited to melanomas (e.g., cutaneous melanoma, metastatic melanomas, and intraocular melanomas), prostate cancer, lymphomas (e.g., cutaneous T-cell lymphoma, mycosis fungicides, Hodgkin's and non-Hodgkin's lymphomas, and primary central nervous system lymphomas), leukemias (e.g., pre-B cell acute lymphoblastic leukemia, chronic and acute lymphocytic leukemia, chronic and acute myelogenous leukemia, adult acute lymphoblastic leukemia, mature B-cell acute lymphoblastic leukemia, prolymphocytic leukemia, hairy cell leukemia, and T-cell chronic lymphocytic leukemia), and metastatic tumors which exhibit these proteins on the cell surface. See Lynn D. Wilson et al., "Cutaneous T-Cell Lymphomas," in CANCER: PRINCIPLES & PRACTICE OF ONCOLOGY 2220-2232 (Vincent T. DeVita, Jr. et al., editors, 5th ed. 1997); Bank et al., 1999, *J. Cutan. Pathol.*, 26(2): 65-71. For example, the cancer may be lung cancer.

Once a tumor is diagnosed in a patient, the first question is whether the tumor has progressed and spread to the regional lymph nodes and to distant organs. In the end, most cancer deaths result from metastases that are resistant to conventional cancer therapies. Metastases can be located in different organs and in different regions of the same organ, making complete eradication by surgery, radiation, drugs, and/or biotherapy nearly impossible. Also contemplated for treatment with the methods, combination therapies, and compositions disclosed herein is the treatment of metastatic cancer. Cancers typically begin their growth in only one location in the tissue of origin. As the cancer progresses, the cancer may migrate to a distal location in the patient. For example, a cancer beginning in the prostate may migrate to the lung. Thus, if a primary tumor is given enough time to go through these steps, it will form metastatic lesions at a site or sites distant to the primary tumor. The reagents, methods, and combination therapies disclosed inhibit or prevent one or more of these steps in the metastatic process. For additional details on the mechanism and pathology of tumor metastasis, see Isaiah J. Fidler, "Molecular Biology of Cancer: Invasion and Metastasis," in CANCER: PRINCIPLES & PRACTICE OF ONCOLOGY 135-152 (Vincent T. DeVita et al., editors, 5th ed., 1997).

Accordingly, one aspect of the invention provides methods of using and compositions comprising ligands to Pgrmc1, which are capable of destabilizing EGFR. A preferred ligand to Pgrmc1 is AG-205. These ligands can be used alone or in combination with other agents or cancer treatment modalities that prevent metastases or inhibit progression of metastatic lesions.

Another aspect of the invention contemplates the use of the ligands in combination with other conventional cancer treatment modalities, in the form of combination therapies. Many treatments exist for cancers. The particular cancer therapy or combination of therapy modalities used to treat a cancer depend greatly on the type of cancer, its stage, the patient (e.g., weight, sex, age, health, prior cancers, and the like), and where the patient is in therapy (e.g., first treatment, in blast crisis, refractive to initial treatments, cancer relapse, or a second cancer perhaps induced by the treatment of the first cancer months or years before). Therefore, physicians will frequently have to combine a variety of treatment modalities that will best suit the needs of the patient in combating the disease and the patient's self-determination of quality of life.

Treatment modalities include but are not limited to surgery, radiation therapy, chemotherapy, biologic therapy (e.g., cytokines, immunotherapy, and interferons), hormone therapies, and hyperthermia. Conventional chemotherapy can be further broken down into hormone therapies (e.g., antiestrogens, aromatase inhibitors, gonadotropin-releasing hormone analogues, and anti-androgens), anti-tumor alkylating agents (e.g., mustards, nitrosoureas, tetrazines, and aziridines), cisplatin and its analogues, anti-metabolites (e.g., methotrexate, antifolates, 5-fluoropyrimidines, cytarabine, azacitidine, gemcitabine, 6-thipurines, and hydroxyurea), topoisomerase interactive agents, antimicrotubule agents (e.g., vinca alkaloids, taxanes, and estramustine), differentiating agents (e.g., retinoids, vitamin D3, polarapolar compounds, butyrate and phenylactetate, cytotoxic drugs, cytokines, and combinations thereof), and other chemotherapeutic agents such as fludarabine, 2-chlorodeoxyadenosine, 2'-deoxycoformycin, homoharringtonine (HHT), suramin, bleomycin, and L-asparaginase.

Treatment of metastases may be with the compositions, combination therapies and methods described herein by themselves or in combination with other cancer treatment modalities depending on the site of the metastases and the primary tumor from which the metastases originates. The most common sites for tumors to metastasize are brain, lung, liver, bone, malignant pleural and pericardial effusions, and malignant ascites.

The lungs are the second most frequent site of metastatic disease. Anatomically, the lungs are vascular rich sites and the first capillary bed encountered by circulating tumor cells as they exit from the venous drainage system of their primary tumor. Thus, the lungs act as the initial filtration site, where disseminated tumor cells become mechanically trapped. However, the cells which get trapped there and go on to proliferate and form metastatic lesions will largely depend upon the original primary tumor from which they derive. This hematogenous process of lung metastases is the most common means, but pulmonary metastases can also occur via the lymphatic system. See Harvey I. Pass et al., "Metastatic Cancer to the Lung," in CANCER: PRINCIPLES & PRACTICE OF ONCOLOGY 2536-2551 (Vincent T. DeVita et al., editors, 5th ed., 1997). The most common primary tumors which go on to have lung metastases include soft tissue sarcoma, colorectal carcinoma, germ cell tumors, osteosarcoma, certain pediatric tumors (e.g., rhabdomyosarcomas, Ewing's sarcomas, Wilm's tumor, liposarcomas, leiomyosarcomas, alveolar sarcomas, synovial sarcomas, fibrosarcomas, neurogenic sarcomas, and epithelial sarcomas), melanoma, renal cell carcinoma, and breast carcinoma. Most of the metastases from these primary tumors are treated surgically. However, some recommend surgery in combination with chemotherapy. For example, germ cell tumors which have metastasized to the lung are treated with surgical resection following curative cisplatin-based combination chemotherapy.

Treatment of lung metastases frequently involves metastasectomy (i.e., surgical removal of the lung metastatic lesion). Thus one aspect of the invention contemplates the use of the disclosed antibodies in combination with conventional therapies, as discussed herein or as known in the art, for the treatment of lung metastases.

Further, the present invention contemplates the use of ligands to Pgrmc1, able to destabilize a receptor tyrosine kinase such as EGFR. These ligands of interest preferably are administered in a physiologically acceptable carrier to a subject. The ligands may be administered in a variety of ways including but not limited to parenteral administration, including subcutaneous (s.c.), subdural, intravenous (i.v.), intramuscular (i.m.), intrathecal, intraperitoneal (i.p.), intracerebral, intraarterial, or intralesional routes of administration, localized (e.g., surgical application or surgical suppository), and pulmonary (e.g., aerosols, inhalation, or powder) and as described further below. Preferably, the ligands are administered intravenously or subcutaneously.

Depending upon the manner of introduction, the ligands may be formulated in various ways. The concentration of therapeutically active ligand in the formulation (i.e., a formulation that is therapeutically effective to the subject to which it was administered) may vary from about 0.01 mg/mL to 1 g/mL. Preferably, the immunoglobulin composition, when administered to a subject in need thereof, reaches a concentration in the blood of the subject to whom it was administered of about 10 μg/mL or more.

Preferably, the ligand is formulated for parenteral administration in a suitable inert carrier, such as a sterile physiological saline solution. The dose administered will be determined by route of administration. Preferred routes of administration include parenteral, subcutaneous, or intravenous administration.

For parenteral administration, the ligands of the invention can be administered as injectable dosages of a solution or suspension of the substance in a physiologically acceptable diluent with a pharmaceutical carrier, which can be a sterile liquid such as water and oils with or without the addition of a surfactant. Other acceptable diluents include oils of animal, vegetable, or synthetic origin, for example, peanut oil, soybean oil, and mineral oil. In general, glycols such as propylene glycol or polyethylene glycol (PEG) are preferred liquid carriers, particularly for injectable solutions. The ligands can be administered in the form of a depot injection or implant preparation, which can be formulated in such a manner as to permit a sustained release of the active ingredient(s).

According to one aspect of the invention, the ligand of interest may be administered alone, or in combination with other agents as discussed above to treat and/or ameliorate a tumor. These reagents can also be used in the preparation of a medicament for use in treating a patient. Administration of other cancer therapeutic agents can occur prior to, concurrent with, or after administration with the immunoglobulin. Administration of the subject immunoglobulins can occur before, during or after surgical treatment, radiotherapy, hormone therapy, immunotherapy, hyperthermia, or other cancer treatment modality. Administration of the subject immunoglobulins can occur daily, weekly, or monthly as needed. Preferably, the immunoglobulins are administered weekly for one or more weeks.

Pharmaceutical compositions comprising the ligands can also include, if desired, pharmaceutically acceptable, non-toxic carriers or diluents, which are vehicles commonly used to formulate pharmaceutical compositions for animal or human administration. The diluent is selected so as not to affect the biological activity of the combination. Examples include but are not limited to distilled water, physiological phosphate-buffered saline, Ringer's solutions, dextrose solution, and Hank's solution.

The agents of the invention can be formulated into preparations for injections by dissolving, suspending or emulsifying them in an aqueous or non-aqueous solvent, such as vegetable or other similar oils, synthetic aliphatic acid glycerides, esters of higher aliphatic acids or propylene glycol. The formulations may also contain conventional additives, such as solubilizers, isotonic agents, suspending agents, emulsifying agents, stabilizers and preservatives.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate)) as described by Langer et al., *J. Biomed. Mater. Res.* 15: 167-277 (1981) and Langer, *Chem. Tech.* 12: 98-105 (1982) or poly(vinylalcohol)), polylactides (U.S. Pat. No. 3,773,919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e., injectable microspheres composed of lactic acid-glycolic acid copolymer and leuprolide acetate), and poly-D-(−)-3-hydroxybutyric acid (EP 133,988).

Sustained-release compositions also include liposomally entrapped ligand. Liposomes containing the ligand are prepared by methods known per se. See, e.g., Epstein et al., Proc. Natl. Acad. Sci. USA 82: 3688-92 (1985); Hwang et al., Proc. Natl. Acad. Sci. USA 77: 4030-4 (1980); U.S. Pat. Nos. 4,485,045; 4,544,545; 6,139,869; and 6,027,726. Ordinarily, the liposomes are of the small (about 200 to about 800 Angstroms), unilamellar type in which the lipid content is greater than about 30 mole percent (mol. %) cholesterol; the selected proportion being adjusted for the optimal ligand therapy.

The ligands of this invention can be administered in a sustained release form, for example a depot injection, implant preparation, or osmotic pump, which can be formulated in such a manner as to permit a sustained release of the active ingredient. Implants for sustained release formulations are well-known in the art. Implants are formulated as microspheres, slabs, etc. with biodegradable or non-biodegradable polymers. For example, polymers of lactic acid and/or glycolic acid form an erodible polymer that are well-tolerated by the host. The implant is placed in proximity of a solid tumor for example, so that the local concentration of active agent is increased at that site relative to the rest of the body.

A typical daily dosage might range from about 1 µg/kg to up to about 200 mg/kg subject weight or more, more preferably from about 0.01 mg/kg to about 150 mg/kg subject weight, more preferably from about 0.1 mg/kg to about 100 mg/kg subject weight, more preferably from about 1 mg/kg to about 75 mg/kg patient weight (and every integer value between these values) depending on the factors mentioned herein. Typically, the clinician will administer immunoglobulin until a dosage is reached that achieves the desired effect. The progress of this therapy can be easily monitored by conventional assays.

Although the present invention has been described in detail with reference to examples below, it is understood that various modifications can be made without departing from the spirit of the invention, and would be readily known to the skilled artisan.

EXAMPLE 1

EGFR is highly expressed in a variety of tumor types, and the preliminary data show that EGFR levels are sustained by Pgrmc1. As a result, Pgrmc1 drives cell proliferation, at least in part via EGFR. Pgrmc1/Hpr6 activates multiple serine-threonine kinases. To test the role of Pgrmc1 in membrane-associated signaling, Pgrmc1 expression was inhibited by transfection with two separate siRNA oligonucleotide duplexes to distinct regions of the PGRMC1 coding sequence. As a control, parallel cultures were transfected with a control siRNA called sicon.

In MDA-MB-468 cells, which over-express EGFR, transfection with siPGR caused a nearly complete inhibition of EGFR levels. This was reflected in a 28-fold decrease in the predominant 180 kDa tyrosine phosphorylated band in MDA-MB-468 cells. As expected, Pgrmc1 levels were almost completely inhibited. The DNA end-binding protein ku70 was used as a control for equal protein loading because no ku70 alterations were detected in these experiments. Pgrmc1 did not affect EGFR transcription, because EGFR transcript levels were unchanged in siPGR-transfected cells, while Pgrmc1 levels decreased.

A second siRNA targeting Pgrmc1 (which we will refer to as siPGR2), attenuated EGFR levels to a lesser extent. Using the siPGR2 siRNA, the levels of the 180 kDa tyrosine phosphorylated band were diminished, while ku70 was unaffected.

EGFR drives proliferation of cancer cells through multiple pathways, and during the sub-culturing of Pgrmc1-inhibited cells, it was immediately evident that the cells had diminished proliferation. When cell growth was tested by a time course, a 36% decrease in proliferation in Pgrmc1-inhibited cells was detected. The decrease in proliferation was highly significant (P=0.0015 at day 5 and 0.0017 at day 8). In this assay, cells in quadruplicate were counted during multiple stages of growth and stained viable cells by trypan blue. The results are representative of a duplicate assay and are consistent with multiple observations during sub-culturing.

The change in proliferation rate between sicon and siPGR-transfected cells was largely blocked with the EGFR inhibitor AG1478. In this assay, cells were transfected with siRNA oligonucleotides, split into 96 well culture dishes and treated with increasing doses of AG1478. Viability was measured using the MTT assay. The results suggest that EGFR contributes to the increased growth rate of Pgrmc1-expressing cells. The data were generated using MDA-MB-468 human breast cancer cells as a model system. The same phenotype in A549 human lung cancer cells was found, which showed decreased EGFR expression after treatment with RNAi to Pgrmc1. In addition, A549 cells demonstrated decreased growth in soft agar when expressing a stable shRNA targeting Pgrmc1. Thus, Pgrmc1 stabilizes EGFR in multiple cell lines from more than one tissue of origin and affects the functional capacity of EGFR.

There are four aromatic ligands for the *Arabidopsis* Pgrmc1 homologue (Yoshitani et al., 2005), which is highly conserved with human Pgrmc1 in the heme-1 domain (Hand et al., 2003). The effect of the Pgrmc1 ligand called AG-205 on EGFR stability and viability was tested. When MDA-MB-468 cells were treated with increasing doses of AG-205, a 12-50 µM dose induced a 14-fold decrease in EGFR levels. In contrast, a 12 µM dose of AG-205 increased Pgrmc1 levels 4.8-fold, while doses of 25 and 50 µM decreased Pgrmc1 to nearly undetectable levels. Ku70 levels were not affected by the AG-205 treatment.

To assure that the results were not unique to the MDA-MB-468 cell line, A549 lung cancer cells were also treated with increasing doses of AG-205. As for MDA-MB-468 cells, AG-205 de-stabilized EGFR in a dose-dependent manner, with 20-50 µM AG-205 having the optimal activity. In contrast, AG-205 had little effect on the stability of the focal adhesion kinase or the Met receptor tyrosine kinase.

Pgrmc1 Ligand Inhibits Cell Growth in Cancer Cells.

A 20 µM dose of AG-205 decreased EGFR levels and inhibited cancer cell viability. The 20 µM dose induced cell rounding and a marked loss of viability in both A549 and MDA-MB-468 cells. The growth inhibitory activity was dependent on the culture conditions, with AG-205 killing cells grown in low serum conditions but not 10% serum. The difference in viability was highly significant under these conditions (P=0.0006 for MDA-MB-468 cells at a dose of 20 µM AG-205). While AG-205 induced a loss of viability, we did not detect an increase in cleavage of the polyADP ribose polymerase (PARP) or caspase 3, suggesting that the cells were dying via an apoptotic mechanism.

When ligand is abundant under normal culture conditions, lower doses of EGFR are sufficient to maintain cell viability. AG-205 caused a slight increase in viability in MDA-MB-468 cells. In MDA-MB-468 cells, EGF treatment induces apoptosis, and it is likely that, by reducing EGFR levels, AG-205 limits EGF-induced apoptosis and has a slight positive effect on viability. The results suggest that inhibiting Pgrmc1 with the AG-205 ligand causes EGFR to be de-stabilized, ultimately leading to cell death.

AG-205 kills cancer cells while Pgrmc1 RNAi does not. This is because RNAi is generally not a complete loss of function, and we were able to detect residual Pgrmc1 transcription following both siRNA and shRNA, although transcription was greatly attenuated. There may also be Pgrmc1 variants expressed that we were unable to detect. Secondly, RNAi inhibits only Pgrmc1, while AG-205 may inhibit the related Pgrmc2 and Neudesin proteins as well. It may be that inhibiting each of these proteins cumulatively results in cell killing.

The Pgrmc1 Ligand AG-205 Mis-Localizes EGFR.

The model shows that Pgrmc1 binds to Cav1 to increase the transport of RTKs to the cell membrane and increase their stability within caveolae once localized to the cell membrane. One prediction of this model is that disrupting Pgrmc1 function will cause RTKs to accumulate in an intermediate state away from the cell membrane.

To test this model, EGFR was stained by immunofluorescence 24 hours after treatment with 20 µM AG-205 in MDA-MB-468 cells. In cells treated with the vehicle control, EGFR localized to the cell membrane. In contrast, EGFR localized to both the cell membrane and an intracellular ring which corresponds to the perinuclear region of the cell. Also, Pgrmc1 may control the uptake from the membrane to the perinuclear region.

Thus, a mechanism has been found by which cancer cells stabilize RTKs and promote proliferation. This pathway is unusual in that the initiating protein is readily targeted by known ligands, and these ligands cause RTKs to be mis-localized initially, subsequently leading to cell death.

Methodology for the Experiments

Tissue culture. MDA-MB-468 cells were a kind gift from Dr. Rina Plattner of the University of Kentucky and were maintained in medium consisting of Dulbecco's Modified Eagle Medium containing 10% serum supreme (Fisher) and antibiotics. Cells were grown at 37° C. in 5% $CO_2$ in air. A549 and HCC827 lung cancer cells, as well as SK-Br-3 breast cancer cells were obtained from the ATCC (American Type Culture Collection) and were grown under the same conditions. The H1650 lung cancer cell line was a kind gift from Dr. Heinz Kohler of the University of Kentucky. The Pgrmc1 ligand AG-205 was purchased from Timtec, Inc. The EGFR inhibitor AG1478 was from Biomol, Inc. and was used at a concentration range of 0.8-40 µM.

RNAi. For shRNA inhibition, the plasmids pGIPZ and V2LHS_90636, which is based on pGIPZ and drives the expression of an shRNA targeting Pgrmc1, were obtained from Open Biosystems, Inc. and purified using a Qiagen Maxi-prep purification kit. Viral vectors were produced by the Viral Vector Core at the Translational Core Laboratories, Cincinnati Children's Hospital Research Foundation, Cincinnati, Ohio. For lentiviral infection, cells were split to a density of 500,000 cells/100 cm dish, allowed to attach overnight, and then were switched to medium containing 0.1% serum and infected with $6.4 \times 10^5$ lentiviral particles in 8 µg/ml polybrene (Chemicon, Inc.) overnight. The cells were then washed in fresh media, selected in 5 µg/ml puromycin for 5 days and checked for green fluorescence microscopically.

Gene inhibition with siRNA transfected using Oligofectamine (Invitrogen) was performed essentially as described (Crudden et al., (2006) *J Pharmacol Exp Ther* 316:448-55; Mallory et al., (2005) Mol Pharmacol 68:1747-56). To target Pgrmc1, an oligonucleotide duplex corresponding to the 21 base pairs after position 509 in the Pgrmc1 open reading frame was used. The duplex is referred to as siPGR (Ambion, cat#16706, part#4392421). A second oligonucleotide duplex targeted a 21 base sequence at position 559 in the Pgrmc1 open reading frame and is referred to as "siPGR2". The control was the "control silencer #1" (Ambion, cat#AM4635).

Immunological techniques. Cells were extracted in RIPA buffer (50 mM Tris, pH 8.0, 1% Nonidet P-40, 150 mM NaCl, 0.5% sodium deoxycholate, 0.1% sodium dodecyl sulfate, 1 mM phenylmethylsulfonyl fluoride, 10 μg/ml of aprotinin, leupeptin and pepstatin) for standard western blotting. The antibodies used in the study were anti-caveolin-1 (N-20, Santa Cruz Biologicals, # sc-894), anti-EGFR (1005, Santa Cruz, # sc-03), anti-ku70 (A-9, Santa Cruz # sc-5309), anti-Met (C-12, Santa Cruz # sc-10), anti-PARP (H-250, Santa Cruz # sc-7150), anti-phosphotyrosine (P-Tyr-100, Cell Signaling), anti-Pgrmc1 (Novus Biologics) and anti-tubulin (Neomarkers). Some western blots for Pgrmc1 were performed with a polyclonal antibody called anti-PGR-UK1 which was raised in rabbits to an internal 10 amino acid peptide.

For immuno-precipitation, cells were plated at a density of 500,000 cells/dish in normal growth medium and left overnight. The next day, the cells were then scraped from the dish, washed in PBS and lysed in 1% NP-40 buffer (1% NP-40, 20 mM Tris, 150 mM NaCl, 5 mM EDTA, 1 mM $Na_3VO_4$, pH 7.4, and 10 μg/ml of the protease inhibitors aprotinin and leupeptin) containing 1 mM $Na_3VO_4$. The lysates were divided into equal portions and immune-precipitated with protein A/G-agarose and various antibodies. After a 3 hour incubation, the agarose was pelleted by centrifugation and washed three times in 1% NP-40 buffer.

Immunofluorescence for EGFR was performed as described previously (Crudden et al., (2005) *Tumour Biol* 26:142-6). Cells were grown on chamber slides, washed and fixed with 3.7% formaldehyde. The cells were then permeabilized with 0.1% Triton X-100 in phosphate-buffered saline, blocked with 10% serum and incubated, in turn, with anti-EGFR 1005 and a Texas red-labeled anti-rabbit secondary antibody.

Proliferation, anchorage-independent growth and migration assays. For growth curves, cells were plated in 24 well dishes and grown in 10% serum-containing medium. At various times, the cells were harvested with trypsin and fixed with formaldehyde added to a final concentration of 3.7%. Following the harvest of the final time point, the cells from each time point were counted using a Bright-line hemocytometer (Hausser Scientific).

MTT viability assays were performed as described previously. Briefly, cells were plated in 96-well tissue culture dishes and grown in various media with different drug doses. The cells were then incubated with 0.5 mg/ml of 3-[4,5-dimethylthiazol-2-y]-2,5-diphenyltetrazolium bromide for 1.5 hours, at which time the media was removed, the precipitated crystals were dissolved in dimethyl sulfoxide, and the absorbance at 590 nm was measured using a Bio-Tek μQuant spectrophotometer.

FACS was performed essentially as described previously (Mallory (2005)). Cells were trypsinized, washed and fixed in 70% ethanol, then stained in 20 μg/ml propidium iodide containing 50 μg/ml DNase-free RNase. FACS analysis was performed at the University of Kentucky flow cytometry facility, and the data were analyzed using Modfit software (Verity, Inc.).

For soft agar assays, cells were resuspended in 0.4% agar in DMEM at a density of 200 cells/ml and overlaid on 1% agar, which was also dissolved in 1×DMEM. Cells were plated in triplicate, and the assay was performed at least two separate times. Cells were grown for approximately 2 weeks and imaged using an Olympus IX70 microscope. The perimeters of 30-35 different colonies were calculated using Pictureframe 2.3 software (Optronics, Inc.).

To assay migration, serum-starved shRNA-expressing cells were suspended in DMEM containing 1% bovine serum albumin and placed in the top well of invasion chambers (BD Biosciences). Medium containing 10% serum was placed in the lower chamber as a chemoattractant. Cells were allowed to invade for 16 hours at 37° C. Cells on the upper surface of the membrane were removed, and cells on the undersurface were fixed, stained with 0.5% crystal violet in 20% methanol and counted.

RT-PCR. Cells were harvested with trypsin, and RNA was purified, reverse transcribed with random hexamers, and amplified using Taq polymerase (GenScript, Piscataway, N.J.) in an Eppendorf Master Cycler (Eppendorf, Westbury, N.Y.) for 28-34 cycles of 94° C. for 1 minute., 55° C. for 1 minute., and 72° C. for 1 minute. PCR reactions contained primers to either EGFR, Pgrmc1, LDLR or PAI1 in combination with primers to actin, which served as an internal control for cDNA loading. The primer sequences for EGFR were EGFR+100F (ACGAGTAACAAGCTCACGCAG (SEQ ID NO: 1)) and EGFR+380R (TGCATCATAGTTA-GATAAGAC (SEQ ID NO: 2)); the primers for PAI1 were PAI+90F (GTGGCCCACCTGGCCTCAGAC (SEQ ID NO: 3))and PAI+360R (GATCGCGTCTGTGGTGCTGA (SEQ ID NO: 4)); and the primers for LDLR were LDLR+100F (TGCCAAGACGGGAAATGCATC (SEQ ID NO: 5)) and LDLR+379R (CGAACTGCCGAGAGATGCAC (SEQ ID NO: 6)). Pgrmc1 was amplified with the primers HPR+1080F and HPR+1370R, which have been described previously (Crudden et al., (2006) *J Pharmacol Exp Ther* 316: 448-55) as have the actin primers (Cance et al., (1992) *Surg Oncol* 1:309-14). PCR products were visualized by electrophoresis in 2% agarose 1000 (Invitrogen).

Sucrose gradient fractionation. Caveolae fractionation was performed essentially as described (Liu et al. (1998) *Biochem Biophys Res Commun* 245:684-90). Cells were washed once with PBS, suspended in Tris lysis buffer (25 mM Tris, pH 7.4, 250 mM sucrose and 2 mM EDTA) and lysed by dounce homogenization, passage through a 25 gauge needle and three rounds of sonication. Lysates were then mixed with MBS buffer (25 mM MES, pH 6.5, 150 mM NaCl and 2 mM EDTA) containing 80% sucrose, mixed and overlaid in a SW41 rotor tube with MBS containing 35% sucrose and 5% sucrose. The gradient was centrifuged for 3 hours at 175,000×g, and 1.2 ml fractions were collected.

Results of the Experiments

Pgrmc1 stabilizes EGFR. Pgrmc1/Hpr6 activates multiple serine-threonine kinases. To test the role of Pgrmc1 in membrane-associated signaling, Pgrmc1 expression was inhibited by transfection with two separate siRNA oligonucleotide duplexes to distinct regions of the Pgrmc1 coding sequence.

In MDA-MB-468 cells, which over-express EGFR, transfection with siPGR caused a nearly complete inhibition of EGFR levels. This was reflected in a 28-fold decrease in the predominant 180 kDa tyrosine phosphorylated band in MDA-MB-468 cells. As expected, Pgrmc1 levels were almost completely inhibited. The DNA end-binding protein ku70 was used as a control for equal protein loading because no ku70 alterations were detected in these experiments. Pgrmc1 did not affect EGFR transcription, because EGFR transcript levels were unchanged in siPGR-transfected cells, while Pgrmc1 levels decreased.

A second siRNA targeting Pgrmc1 (which we will refer to as siPGR2), attenuated EGFR levels to a lesser extent. Using the siPGR2 siRNA, the levels of the 180 kDa tyrosine phosphorylated band were diminished, while ku70 was unaffected.

EGFR drives proliferation of cancer cells through multiple pathways, and we detected a 36% decrease in proliferation in Pgrmc1-inhibited cells. The decrease in proliferation was highly significant ($P=0.0015$ at day 5 and 0.0017 at day 8). The change in proliferation rate between siCON and siPGR-transfected cells was largely blocked with the EGFR inhibitor AG1478, suggesting that EGFR contributes to the increased growth rate of Pgrmc1-expressing cells.

Pgrmc1 stabilizes EGFR in lung cancer cells. In A549 lung cancer cells, Pgrmc1 inhibition by shRNA caused a 4.1-fold reduction in EGFR levels, with no change in Met. As expected, Pgrmc1 levels were inhibited, but tubulin levels were not. Reduced EGFR levels could arise from altered transcription or post-transcriptional events. However, EGFR transcript levels were unchanged after Pgrmc1 was inhibited.

The shPGR short hairpin targeted a sequence in the end of the 3' untranslated region of the Pgrmc1 transcript. A549 cells infected with the Lv-shPGR lentivirus were transfected with either a control plasmid or a plasmid expressing a form of Pgrmc1 that lacked the 3' untranslated region (Pgrmc1Δ3'). A549 cells transfected with the control plasmid maintained a low level of EGFR, while EGFR was elevated in cells expressing Pgrmc1Δ3', which was confirmed by western blot. Thus, EGFR levels are dependent on Pgrmc1 expression.

EGFR promotes growth and adhesion of lung cancer cells, and we tested the extent to which these properties were altered when Pgrmc1 was inhibited. A549/GIPZ and A549/shPGR cells grew at equivalent rates, and we did not detect any change in their cell cycle profile by FACS analysis. In contrast, growth in soft agar differed markedly between the two cell populations. A549/GIPZ cells readily formed colonies in soft agar, while A549/shPGR cells formed small microcolonies that failed to proliferate. The radii of 30 colonies from each cell population were measured, and A549/GIPZ colonies were 2.9-fold larger, a difference that was highly significant ($P=6\times10^{-13}$, t-test). A box plot of the data in In addition, migration in A549/GIPZ cells was 4.4-fold higher than that of A549/shPGR cells, an effect that was highly significant (P=0.002, t-test). Thus, Pgrmc1 increases anchorage independent growth and migration.

A Pgrmc1 ligand inhibits EGFR stability. There are four aromatic ligands for the *Arabidopsis* Pgrmc1 homologue, which is highly conserved with human Pgrmc1 in the heme-1 domain. The effect of the Pgrmc1 ligand called AG-205 on EGFR stability and viability was tested. When MDA-MB-468 cells were treated with increasing doses of AG-205, a 12-50 μM dose induced a 14-fold decrease in EGFR levels. In contrast, a 12 μM dose of AG-205 increased Pgrmc1 levels 4.8-fold, while doses of 25 and 50 μM decreased Pgrmc1 to nearly undetectable levels. Ku70 levels were not affected by the AG-205 treatment. The results were not specific for MDA-MB-468 cells, because EGFR was also inhibited by AG-205 in A549 cells, while tyrosine kinase FAK and ku70 were unaffected.

A 20 μM dose of AG-205 inhibited cancer cell viability 72-96 hours after treatment. The 20 μM dose induced cell rounding and a marked loss of viability in both MDA-MB-468 and A549 cells. The growth inhibitory activity was dependent on the culture conditions, with AG-205 killing cells grown in low serum conditions but not 10% serum. The difference in viability was highly significant under these conditions (P=0.0006 for MDA-MB-468 cells at a dose of 20 μM AG-205). While AG-205 induced a loss of viability, we did not detect an increase in cleavage of the polyADP ribose polymerase (PARP) or caspase 3, suggesting that the cells were dying via an apoptotic mechanism.

Because AG-205 inhibited EGFR levels and cell viability, the extent to which the two effects were related was tested. A549 cells were treated with the EGFR inhibitor AG-1478, alone or in combination with AG-205. AG-1478 induced a 25% decrease in viability, while AG-205 was toxic to 47% of the cells, and the combination of the two drugs was not significantly different from that of AG-205 (P=0.31, t-test). The results support the model that AG-1478 and AG-205 function through a common mechanism, which includes EGFR. The toxicity of AG-205 is also dependent on Pgrmc1, because Pgrmc1-inhibited A549 cells exhibited decreased toxicity to AG-205 (P=0.0001, t-test). This experiment was analyzed after 36 hours, and after a longer incubation, both cell types exhibited loss of viability.

Structural features of EGFR appear to be important for the growth inhibiting activity of AG-205. In A549 and MDA-MB-468 cells, AG-205 efficiently inhibited cell growth, and both cell lines express the wild-type form of EGFR (Table 1). NIH-3T3 cells also express the wild-type EGFR and were inhibited by AG-205 (Table 1). In contrast, HCC827 and H1650 cells, which express a ΔE746-A750 deletion mutant of EGFR, were relatively insensitive to AG-205 inhibition (Table 1). SK-Br-3 cells, which express modest amounts of EGFR but extremely high levels of HER2/neu, were also relatively insensitive to AG-205 (Table 1). The results suggest that, in the cell lines tested, alterations in EGFR activation or binding partners can overcome AG-205 sensitivity.

The model is that high EGFR expression is required for maintaining viability under low serum conditions, perhaps via paracrine signaling. When ligand is abundant under normal culture conditions, lower doses of EGFR are sufficient to maintain cell viability. Interestingly, AG-205 caused a slight increase in viability in MDA-MB-468 cells. In MDA-MB-468 cells, EGF treatment induces apoptosis (Armstrong et al., (1994) *Cancer Res* 54:5280-3), and it is likely that, by reducing EGFR levels, AG-205 limits EGF-induced apoptosis and has a slight positive effect on viability.

Pgrmc1 maintains EGFR at the cell membrane, and the localization of EGFR in AG-205-treated cells after 24 hours was tested. Surprisingly, EGFR localized to the perinuclear region of the cell, similar to its localization after RNAi inhibition.

TABLE I

| IC$_{50}$ values for AG-205 in various cell lines | | | |
|---|---|---|---|
| Cell line | Tissue of origin | Serum-starved (μM) | EGFR |
| A431 | epitheloid | 8 | wild-type |
| MDA-MB-231 | breast | 18 | wild-type |
| MDA-MB-468 | breast | 12 | wild-type |
| A549 | lung | 15 | wild-type |
| H157 | lung | 10 | wild-type |
| H358 | lung | 12 | wild-type |
| H1650 | lung | >100 | ΔE746-A750 |
| HCC827 | lung | >100 | ΔE746-A750 |

It will be appreciated that, although specific embodiments of the invention have been described herein for purposes of illustration, various modifications may be made without departing from the spirit and the scope of the invention. Accordingly, the invention is not limited except as by the appended claims.

What is claimed is:

1. A method for inhibiting growth of a tumor and/or metastatic progression thereof in a human subject in need thereof comprising administering a compound named AG-205 consisting of the following formula to the human subject in need thereof in an amount sufficient to inhibit growth of the tumor and/or metastatic progression thereof,
wherein the tumor comprises breast cancer cells overexpressing progesterone receptor membrane component-1 and wild type epidermal growth factor receptor, wherein AG-205 destabilizes the epidermal growth factor receptor.

2. The method of claim 1, wherein the tumor is a primary tumor or a metastatic lesion.

3. The method of claim 1, wherein the subject is administered AG-205 in an amount of 0.1 mg/kg subject weight to 100 mg/kg subject weight.

4. The method of claim 1, wherein the metastatic progression is to brain, lung, liver, or bone.

5. A method for inhibiting growth of a tumor and/or metastatic progression thereof in a human subject in need thereof comprising administering a compound named AG-205 consisting_of the following formula to the human subject in need thereof in an amount sufficient to inhibit growth of the tumor and/or metastatic progression thereof, administering a chemotherapeutic agent, and further administering an immunotherapeutic agent and/or radiation therapy, wherein the tumor comprises breast cancer cells over-expressing progesterone receptor membrane component-1 and wild type epidermal growth factor receptor, and wherein the AG-205 destabilizes the epidermal growth factor receptor.

6. The method of claim 5, wherein AG-205 is administered intravenously, intrathecally, or subcutaneously to the subject in need thereof.

7. The method of claim 5, wherein AG-205 is administered in an amount of 1 mg/kg subject weight to 100 mg/kg subject weight.

8. The method of claim 5, wherein AG-205 is administered daily, weekly, or monthly.

* * * * *